United States Patent

Schnabel et al.

[11] Patent Number: 5,854,179
[45] Date of Patent: Dec. 29, 1998

[54] SULFUR-SUBSTITUTED PHENYLSULFONYLUREAS, PROCESSES FOR THEIR PREPARATION AND THEIR USE AS HERBICIDES AND PLANT GROWTH REGULATORS

[75] Inventors: Gerhard Schnabel, Grosswallstadt; Lothar Willms, Hofheim; Klaus Bauer, Hanau; Hermann Bieringer, Eppstein; Christopher Rosinger, Hofheim, all of Germany

[73] Assignee: Hoechst Schering AgrEvo GmbH, Berlin, Germany

[21] Appl. No.: 552,670

[22] Filed: Nov. 3, 1995

[30] Foreign Application Priority Data

Nov. 7, 1994 [DE] Germany ............ 44 39 676.7

[51] Int. Cl.⁶ .......................... C07D 403/12; A01N 43/54
[52] U.S. Cl. .......................... 504/214; 504/215; 504/197; 544/321; 544/323; 544/324; 544/331; 544/332; 544/138; 544/296; 544/295; 544/122; 544/123; 544/82; 544/243; 540/601
[58] Field of Search .................... 504/214, 215, 504/197; 544/321, 323, 324, 331, 332, 138, 296, 295, 82; 540/601

[56] References Cited

U.S. PATENT DOCUMENTS

| 4,310,346 | 1/1982 | Levitt et al. | 544/113 |
| 4,369,058 | 1/1983 | Levitt | 544/320 |
| 4,632,695 | 12/1986 | Schurter et al. | 544/211 |
| 4,664,695 | 5/1987 | Schurter et al. | 544/323 |
| 4,892,946 | 1/1990 | Levitt | 544/321 |
| 4,981,509 | 1/1991 | Hillemann | 544/211 |

FOREIGN PATENT DOCUMENTS

| 0 001 515 | 4/1979 | European Pat. Off. . |
| 0 007 687 | 2/1980 | European Pat. Off. . |
| 0 023 141 | 1/1981 | European Pat. Off. . |
| 0 030 138 | 6/1981 | European Pat. Off. . |
| 0 084 020 | 7/1983 | European Pat. Off. . |
| 0 116 518 | 8/1984 | European Pat. Off. . |
| 0 192 489 | 8/1986 | European Pat. Off. . |
| 42 36 902 | 5/1994 | France . |

OTHER PUBLICATIONS

English Language translation of German Patent No. 42 36 902 dated May 5, 1994, to Hoechst Ag.

*Primary Examiner*—John M. Ford
*Attorney, Agent, or Firm*—Frommer Lawrence & Haug LLP

[57] ABSTRACT

Sulfur-substituted phenylsulfonylureas; processes for their preparation and their use as herbicides and plant growth regulators Compounds of the formula (I) and salts thereof

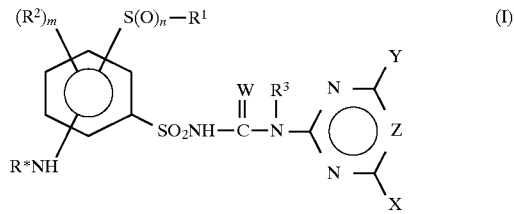

in which $R^*$, $R^1$, $R^2$, $R^3$, X, Y, Z, W, n and m are defined as in claim 1, and specifically $R^*$ is a formyl equivalent of the formula CHO, —CH=NR or $CH(X^1R')(X^2R'')$, are suitable as herbicides and plant growth regulators. They are prepared analogously to known methods, in some cases using novel intermediate products of the formula (XVII)

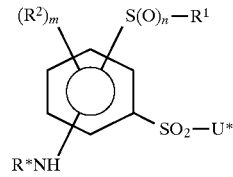

in which $U^*$=$NH_2$, Cl or (substituted) amino.

6 Claims, No Drawings

SULFUR-SUBSTITUTED PHENYLSULFONYLUREAS, PROCESSES FOR THEIR PREPARATION AND THEIR USE AS HERBICIDES AND PLANT GROWTH REGULATORS

DESCRIPTION

Sulfur-substituted phenylsulfonylureas; processes for their preparation and their use as herbicides and plant growth regulators.

The invention relates to the technical field of herbicides and plant growth regulators, in particular herbicides for selective control of broad-leaved weeds and graminaceous weeds in crops of useful plants.

It is known that phenylsulfonylureas which have heterocyclic substituents and carry an amino or a functionalized amino group or a sulfur substituent on the phenyl ring have herbicidal and plant growth regulating properties (EP-A-1515; EP-A-7687; EP-A-30138; U.S. Pat. No. 4,892,946; U.S. Pat. No. 4,981,509, U.S. Pat. No. 4,664,695; U.S. Pat. No. 4,632,695, EP-A-116518; EP-A-23141 (=U.S. Pat. No. 4,310,346); U.S. Pat. No. 4,369,058; EP-A-84020; EP-A-192489; DE 42 36 902 Al).

Surprisingly, it has now been found that certain phenylsulfonylureas with heterocyclic substituents are particularly suitable as herbicides and plant growth regulators.

The present invention relates to compounds of the formula (I) and salts thereof

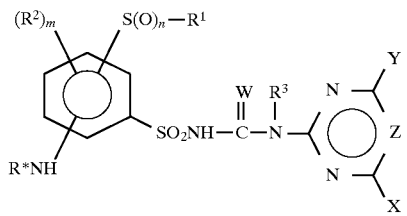

in which

W is an oxygen atom or a sulfur atom, m is 0, 1, 2 or 3, n is 0, 1 or 2,

R is a radical of the formula —CHO, —CH=N—R or

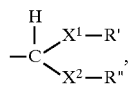

R is H, OH, alkyl, alkenyl, alkynyl, alkoxy, alkenyloxy or alkynyloxy, where each of the last 6 radicals mentioned is unsubstituted or substituted, or is phenyl, which is unsubstituted or substituted, or acyl, amino or mono- or disubstituted amino, $X^1$ is O, S, NH or —N(alkyl)-, $X^2$ is O, S, NH or —N(alkyl)-, R' and R" independently of one another are hydrogen, alkyl, alkenyl or alkynyl, where each of the last 3 radicals mentioned is unsubstituted or substituted by alkoxy, alkylthio or halogen, or together are $(C_2-C_4)$ alkylene or $(C_2-C_4)$alkenylene, $R^1$ is hydroxyl, amino, mono- or disubstituted amino, hydroxylamino, substituted hydroxylamino, hydrazino, substituted hydrazino, an aliphatic hydrocarbon or hydrocarbonoxy radical or aryl, heteroaryl, aryloxy or heteroaryloxy, where each of the last 6 radicals mentioned is unsubstituted or substituted, $R^2$ is halogen, CN, $NO_2$, amino, mono- or disubstituted amino, alkyl or alkoxy, where each of the last two radicals mentioned is unsubstituted or substituted, $R^3$ is hydrogen, hydroxyl, $(C_1-C_4)$alkyl, $(C_1-C_4)$alkoxy, $(C_2-C_4)$alkenyl or $(C_2-C_4)$alkynyl, where each of the last 4 radicals mentioned is unsubstituted or substituted by halogen, preferably F, Cl or Br, X and Y independently of one another are hydrogen, hydroxyl, amino, mono- or disubstituted amino, alkyl, cycloalkyl, alkenyl, alkynyl, alkoxy, alkenyloxy, alkynyloxy, cycloalkoxy or alkylthio, where each of the last 9 radicals mentioned is unsubstituted or substituted, and z is CH, N

in which $R^0$ is halogen, cyano, alkyl, alkoxy, haloalkyl or haloalkoxy.

In formula (I) and all the formulae below, the alkyl, alkoxy, haloalkyl, haloalkoxy, alkylamino and alkylthio radicals and the corresponding unsaturated and/or substituted radicals can in each case be straight-chain or branched in the carbon skeleton. Unless specifically stated, the lower carbon skeletons, for example having 1 to 6 carbon atoms, or in the case of unsaturated groups having 2 to 6 carbon atoms, are preferred for these radicals. Alkyl radicals, including in the composite meanings, such as alkoxy, haloalkyl and the like, are, for example, methyl, ethyl, n- or i-propyl, n-, i-, t- or 2-butyl, pentyl radicals, hexyl radicals, such as n-hexyl, i-hexyl and 1,3-dimethylbutyl, or heptyl radicals, such as n-heptyl, 1-methylhexyl and 1,4-dimethylpentyl; alkenyl and alkynyl radicals have the meaning of the possible unsaturated radicals corresponding to the alkyl radicals; alkenyl is, for example, allyl, 1-methyl-prop-2-en-1-yl, 2-methyl-prop-2-en-1-yl, but-2-en-1-yl, but-3-en-1-yl, 1-methyl-but-3-en-1-yl and 1-methyl-but-2-en-1-yl; and alkynyl is, for example, propargyl, but-2-yn-1-yl, yl, but-3-yn-1-yl and 1-methyl-but-3-yn-1-yl.

Halogen is, for example, fluorine, chlorine, bromine or iodine. Haloalkyl, -alkenyl and -alkynyl are alkyl, alkenyl or alkynyl, respectively, which are partly or completely substituted by halogen, preferably by fluorine, chlorine and/or bromine, in particular by fluorine or chlorine, for example $CF_3$, $CHF_2$, $CH_2F$, $CF_3CF_2$, $CH_2FCHCl$, $CCl_3$, $CHCl_2$ and $CH_2CH_2Cl$; haloalkyl is, for example, $OCF_3$, $OCHF_2$, $OCH_2F$, $CF_3CF_2O$, $OCH_2CF_3$ and $OCH_2CH_2Cl$; the corresponding applies to haloalkenyl and other radicals substituted by halogen.

A hydrocarbon radical is a straight-chain, branched or cyclic and saturated or unsaturated aliphatic or aromatic hydrocarbon radical, for example alkyl, alkenyl, alkynyl, cycloalkyl, cycloalkenyl or aryl; aryl here is a mono-, bi- or polycyclic aromatic system, for example phenyl, naphthyl, tetrahydronaphthyl, indenyl, indanyl, pentalenyl, fluorenyl and the like, preferably phenyl; a hydrocarbon radical is preferably alkyl, alkenyl or alkynyl having up to 12 carbon atoms or cycloalkyl having 3, 4, 5, 6 or 7 ring atoms or phenyl; the corresponding definition applies to a hydrocarbon radical in a hydrocarbonoxy radical.

A heterocyclic radical or ring (heterocyclyl) can be saturated, unsaturated or heteroaromatic; it preferably contains one or more hetero units in the ring, preferably from the group consisting of N, O, S, SO and $SO_2$; preferably, it is an aliphatic heterocyclyl radical having 3 to 7 ring atoms or a heteroaromatic radical having 5 or 6 ring atoms and contains 1, 2 or 3 hetero units. The heterocyclic radical can be, for example, a heteroaromatic radical or ring (heteroaryl), such as, for example, a mono-, bi- or polycyclic aromatic system in which at least 1 ring contains one or more hetero atoms, for example pyridyl, pyrimidinyl, pyridazinyl, pyrazinyl, thienyl, thiazolyl, oxazolyl, furyl, pyrrolyl, pyrazolyl and imidazolyl, or is a partly hydrogenated radical, such as oxiranyl, pyrrolidyl, piperidyl, piperazinyl, dioxolanyl, morpholinyl or tetrahydrofuryl. Possible substituents for a substituted heterocyclic radical are the substituents mentioned below, and in addition also oxo. The oxo groups can also occur on the hetero ring atoms which can exist in different oxidation levels, for example in the case of N and S.

Substituted radicals, such as substituted hydrocarbon radicals, for example substituted alkyl, alkenyl, alkynyl, aryl, phenyl and benzyl, or substituted heterocyclyl or heteroaryl, are, for example, a substituted radical derived from the unsubstituted parent substance, the substituents being, for example, one or more, preferably 1, 2 or 3, radicals from the group consisting of halogen, alkoxy, haloalkoxy, alkylthio, hydroxyl, amino, nitro, carboxy, cyano, azido, alkoxycarbonyl, alkylcarbonyl, formyl, carbamoyl, mono- and dialkylaminocarbonyl, substituted amino, such as acylamino and mono- and dialkylamino, and alkylsulfinyl, haloalkylsulfinyl, alkylsulfonyl, haloalkylsulfonyl and, in the case of cyclic radicals, also alkyl and haloalkyl, as well as unsaturated aliphatic radicals corresponding to the saturated hydrocarbon-containing radicals mentioned, such as alkenyl, alkynyl, alkenyloxy, alkynyloxy and the like. In the case of radicals with carbon atoms, those having 1 to 4 carbon atoms, in particular 1 or 2 carbon atoms, are preferred. Substituents from the group consisting of halogen, for example fluorine and chlorine, $(C_1-C_4)$alkyl, preferably methyl or ethyl, $(C_1-C_4)$haloalkyl, preferably trifluoromethyl, $(C_3-C_4)$alkoxy, preferably methoxy or ethoxy, $(C_1-C_4)$haloalkoxy, nitro and cyano, are as a rule preferred. The substituents methyl, methoxy and chlorine are particularly preferred here.

Mono- or disubstituted amino is a chemically stable radical from the group consisting of substituted amino radicals which are N-substituted, for example, by one or two identical or different radicals from the group consisting of alkyl, alkoxy, acyl and aryl; preferably monoalkylamino, dialkylamino, acylamino, arylamino, N-alkyl-N-arylamino and N-heterocyclic radicals; alkyl radicals having 1 to 4 carbon atoms are preferred here; aryl here is preferably phenyl or substituted phenyl; the definition given below applies here to acyl, preferably $(C_1-C_4)$alkanoyl. A corresponding definition applies to substituted hydroxylamino or hydrazino.

Optionally substituted phenyl is preferably phenyl which is unsubstituted or mono- or polysubstituted, preferably up to three times, by identical or different radicals from the group consisting of halogen, $(C_1-C_4)$alkyl, $(C_1-C_4)$alkoxy, $(C_1-C_4)$halogenalkyl, $(C_1-C_4)$halogenalkoxy and nitro, for example o-, m- and p-tolyl, dimethylphenyl radicals, 2-, 3- and 4-chlorophenyl, 2-, 3- and 4-trifluoro- and -trichlorophenyl, 2,4-, 3,5-, 2,5- and 2,3-dichlorophenyl and o-, m- and p-methoxyphenyl.

An acyl radical is the radical of an organic acid, for example the radical of a carboxylic acid and radicals of acids derived therefrom, such as the thiocarboxylic acid, optionally N-substituted iminocarboxylic acids or the radical of carbonic acid monoesters, optionally N-substituted carbamic acid, sulfonic acids, sulfinic acids, phosphonic acids and phosphinic acids. Acyl is, for example, formyl, alkylcarbonyl, such as $(C_1-C_4-\text{alkyl})$carbonyl, phenylcarbonyl, in which the phenyl ring can be substituted, for example as shown above for phenyl, or alkoxycarbonyl, phenyloxycarbonyl, benzyloxycarbonyl, alkylsulfonyl, alkylsulfinyl, N-alkyl-1-iminoalkyl and other radicals of organic acids.

The above examples of general terms, such as alkyl, acyl, aryl, substituted radicals and the like, are not a complete list; in particular the terms also include meanings of the same type which are given below for the preferred compounds.

The invention also relates to all the stereoisomers included by the formula (I) and mixtures thereof. Such compounds of the formula (I) contain one or more asymmetric carbon atoms or also double bonds which are not shown separately in the general formula (I). The possible stereoisomers defined by their specific spatial form, such as enantiomers, diastereomers and Z and E isomers, are all included by the formula (I) and can be obtained from mixtures of the stereoisomers by customary methods or else prepared by stereoselective reactions in combination with the use of stereochemically pure starting substances.

The compounds of the formula (I) can form salts in which the hydrogen of the $—SO_2—NH—$ group is replaced by a cation suitable for agriculture. These salts are, for example, metal salts, in particular alkali metal salts or alkaline earth metal salts, in particular sodium and potassium salts, or else ammonium salts or salts with organic amines.

Compounds of the formula (I) according to the invention or salts thereof which are of particular interest are those in which R* is a radical of the formula —CHO, —CH=N—R or

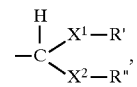

R is H, OH, $NH_2$, $(C_1-C_6)$alkyl, $(C_1-C_6)$haloalkyl, $(C_1-C_6)$alkoxy, $(C_1-C_6)$haloalkoxy, phenyl, which is unsubstituted or substituted, or $[(C_1-C_3)\text{alkyl}]$-carbonyl, $[(C_1-C_3)\text{alkoxy}]$carbonyl, aminocarbonyl, methylaminocarbonyl, dimethylaminocarbonyl, mono- or $\text{di}[(C_1-C_6)\text{alkyl}]$amino, $[(C_1-C_3)\text{alkyl}]$ carbonylamino, $[(C_1-C_3)\text{alkoxy}]$carbonylamino, aminocarbonylamino, methylaminocarbonylamino, dimethylaminocarbonylamino, preferably H or $(C_1-C_4)$alkyl, $X^1$ is an oxygen atom, $X^2$ is an oxygen atom and R' and R" independently of one another are $(C_1-C_4)$alkyl.

Compounds of the formula (I) according to the invention which are of particular interest are those in which $R^1$ is OH, $NR^4R^5$, $(C_1-C_6)$alkyl, $(C_2-C_6)$alkenyl, $(C_2-C_6)$alkynyl, $(C_1-C_6)$alkoxy, $(C_2-C_6)$alkenoxy, $(C_2-C_6)$alkynoxy, $(C_3-C_7)$cycloalkyl, $(C_3-C_7)$cycloalkoxy, $(C_3-C_7)$cycloalkyl$(C_1-C_2)$alkyl, $(C_3-C_7)$cycloalkyl$(C_1-C_4)$alkoxy, phenoxy, phenyl, thienyl or pyridyl, where each of the last fifteen radicals mentioned is unsubstituted or substituted by one or more radicals from the group consisting of halogen, $(C_1-C_4)$alkoxy, $(C_1-C_4)$haloalkyl, $(C_2-C_4)$alkenoxy, $(C_2-C_4)$haloalkenoxy, $(C_2-C_4)$alkynoxy, $(C_2-C_4)$haloalkynoxy, CN, $NO_2$, $N_3$SCN, OCN, OH, $NR^6R^7$, $CO—R^8$, $(C_1-C_4)$alkylthio, $(C_1-C_4)$haloalkylthio, unsubstituted and substituted phenyl, SO—$R^9$ and $SO_2R^{10}$, and in the case of cyclic radicals also $(C_1-C_4)$alkyl and $(C_1-C_4)$haloalkyl, $R^2$ is halogen, $(C_1-C_3)$alkyl, $(C_1-C_3)$haloalkyl, $(C_1-C_5)$ alkoxyalkyl, $NO_2NR^{11}R^{12}$, CN, $(C_1-C_3)$alkoxy or $(C_1-C_3)$haloalkoxy, $R^3$ is H, OH, $(C_1-C_3)$alkyl, $(C_2-C_3)$alkenyl, $(C_2-C_3)$ alkynyl or $(C_1-C_3)$alkoxy, preferably H or $(C_1-C_4)$ alkyl, $R^4$ is H, OH, $NH_2$, mono- and di[$(C_1-C_3)$alkyl]amino, $(C_1-C_4)$alkyl, $(C_2-C_4)$alkenyl, $(C_2-C_4)$alkynyl, $(C_1-C_4)$alkoxy, $(C_2-C_4)$alkenoxy, $(C_2-C_4)$alkynoxy, where each of the last eight radicals mentioned is unsubstituted or substituted by one or more radicals from the group consisting of halogen, $(C_1-C_3)$alkoxy, $(C_1-C_3)$haloalkoxy, $(C_1-C_3)$alkylthio and $(C_1-C_3)$ haloalkylthio, and $R^5$ is H, $(C_1-C_4)$alkyl, $(C_2-C_4)$alkenyl, $(C_2-C_4)$alkynyl, [$(C_1-C_4)$alkyl]carbonyl, [$(C_2-C_4)$alkenyl]carbonyl, [$(C_1-C_4)$alkoxy]carbonyl, [$(C_2-C_4)$alkenoxy]carbonyl, [$(C_1-C_4)$alkyl]aminocarbonyl, di[$(C_1-C_4)$alkyl] aminocarbonyl, $(C_1-C_4)$alkylsulfonyl, $(C_2-C_4)$ alkenylsulfonyl, $(C_3-C_4)$alkylaminosulfonyl or di[$(C_1-C_4)$alkyl]aminosulfonyl, where each of the last thirteen radicals mentioned is unsubstituted or substituted by one or more radicals from the group consisting of halogen, OH, $(C_1-C_3)$alkoxy, $(C_1-C_3)$haloalkoxy, $(C_1-C_3)$alkylthio and $(C_1-C_3)$haloalkylthio, or $NR^4R^5$ together is a heterocyclic radical which, in addition to the N atom, can contain further hetero units from the group consisting of O, N, S, SO and $SO_2$ in the ring skeleton and which is unsubstituted or substituted by one or more radicals from the group consisting of the oxo function, halogen, OH, $NH_2$, $NO_2$, $NHCH_3$, $N(CH_3)_2$CN, $CONH_2$, $CONHCH_3$, CO—$OCH_3$, CON $(CH_3)_2$, $COCH_3$, CO—H, $(C_1-C_3)$alkyl, $(C_1-C_3)$ haloalkyl, $(C_1-C_3)$alkoxy and $(C_1-C_3)$haloalkoxy, $R^6$ is H, $(C_1-C_4)$alkyl, $(C_1-C_4)$haloalkyl, $(C_2-C_4)$alkenyl, $(C_2-C_4)$haloalkenyl, $(C_2-C_4)$alkynyl, $(C_2-C_4)$ haloalkynyl, OH, $(C_1-C_3)$alkoxy or $(C_2-C_3)$ haloalkoxy and $R^7$ is H, $(C_1-C_4)$alkyl, $(C_1-C_4)$haloalkyl, $(C_2-C_4)$alkenyl, $(C_2-C_4)$haloalkenyl, $(C_2-C_4)$alkynyl, $(C_2-C_4)$ haloalkynyl, CO—H, $CO_2CH_3$, CO—$CH_3$, CO—$NH_2$, CO—$NHCH_3$ or $CON(CH_3)_2$, or $NR^6R^7$ together is a heterocyclic radical which, in addition to the N atom, can contain further hetero units from the group consisting of O, N, S, SO and $SO_2$ in the ring skeleton and which is unsubstituted or substituted by one or more radicals from the group consisting of halogen, OH, $NH_2$, $NO_2$, $CONHCH_3$, $CONH_2$, $NHCH_3$, $N(CH_3)_2$, CN, $CO_2CH_3$, $CON(CH_3)_2$, $COCH_3$, CO—H, $(C_1-C_3)$alkyl, $(C_1-C_3)$haloalkyl, $(C_1-C_3)$alkoxy, $(C_1-C_3)$haloalkoxy and the oxo function, $R^8$ is H, $(C_1-C_3)$alkyl, $(C_1-C_3)$haloalkyl, $(C_1-C_3)$alkoxy, $(C_1-C_3)$haloalkoxy, $(C_1-C_3)$alkylthio, $(C_1-C_3)$ haloalkylthio, $NH_2$, $NHCH_3$, $N(CH_3)_2$ or OH, $R^9$ is $(C_1-C_4)$alkyl, $(C_1-C_4)$haloalkyl, $(C_2-C_5)$ alkoxyalkyl, $(C_2-C_4)$alkenyl, $(C_2-C_4)$haloalkenyl, $(C_2-C_4)$alkynyl or $(C_2-C_4)$haloalkynyl, $R^{10}$ is $(C_1-C_4)$alkyl, $(C_1-C_4)$haloalkyl, $(C_2-C_4)$alkenyl, $(C_2-C_5)$haloalkyl, $(C_3-C_4)$alkoxy, $(C_1-C_4)$haloalkoxy, $(C_2-C_4)$alkenoxy, $(C_2-C_4)$haloalkenoxy, $NH_2$, mono- or di[$(C_1-C_4)$alkyl]amino, $R^{11}$ is H, $(C_1-C_3)$alkyl, $(C_1-C_3)$haloalkyl, $(C_1-C_3)$ alkoxy, $(C_1-C_3)$haloalkoxy or OH and $R^{12}$ is H, $(C_1-C_3)$alkyl, $(C_1-C_3)$haloalkyl, CHO, $COCH_3$, $CO_2CH_3$, $CO_2C_2H_5$, $SO_2CH_3$ or CN, or $NR^{11}R^{12}$ together is a heterocyclic radical which, in addition to the N atom, can contain further hetero units from the group consisting of O, N, S, SO and $SO_2$ in the ring skeleton and is unsubstituted or substituted by one or more radicals from the group consisting of halogen, OH, $NH_2$, $NO_2$, $NHCH_3$, $N(CH_3)_2$, CN, $CONHCH_3$, $CO_2CH_3$, $COCH_3$, $CON(CH_3)_2$, CO—H, $(C_1-C_3)$ alkyl, $CONH_2$, $(C_1-C_3)$alkoxy, $(C_1-C_3)$haloalkyl, $(C_1-C_3)$haloalkoxy and the oxo function, X and Y independently of one another are H, halogen, $(C_1-C_6)$alkyl, $(C_1-C_6)$alkoxy, $(C_1-C_6)$alkylthio, $(C_3-C_7)$cycloalkyl, $(C_2-C_6)$alkenyl, $(C_2-C_6)$alkynyl, $(C_2-C_6)$alkynyloxy or mono- or di[$(C_1-C_4)$alkyl] amino, where each of the last nine radicals mentioned is unsubstituted or substituted by one or more radicals from the group consisting of halogen, $(C_1-C_4)$alkoxy, $(C_1-C_4)$haloalkoxy, $(C_1-C_4)$alkylthio and $(C_1-C_4)$ haloalkylthio, and Z is CH or N.

Compounds of the formula (I) according to the invention and salts thereof which are preferred are those in which $R^1$ is $(C_1-C_4)$alkyl, $(C_2-C_4)$alkenyl, $(C_2-C_4)$alkynyl or $(C_1-C_4)$alkoxy, where each of the last 4 radicals mentioned is unsubstituted or substituted by one or more radicals from the group consisting of halogen, $(C_1-C_4)$ alkoxy and $(C_1-C_4)$alkylthio, or is $(C_3-C_6)$cycloalkyl, benzyl, phenyl, thienyl or pyridyl, where each of the last 5 radicals mentioned is unsubstituted or substituted by one or more radicals from the group consisting of halogen, $(C_1-C_4)$alkyl, $(C_1-C_4)$alkoxy, $(C_1-C_4)$ haloalkyl, $(C_1-C_4)$haloalkoxy, CN, $NO_2$ and OH, or is $NH_2$ or mono- or di[$(C_1-C_4)$alkyl]amino and n is 0, 1 or 2.

Compounds of the formula (I) according to the invention and salts thereof which are preferred are also those in which $R^2$ is $(C_1-C_4)$alkyl, $(C_1-C_4)$alkoxy or halogen and m is 0, 1, 2 or 3, preferably 0 or 1.

Compounds of the formula (I) according to the invention and salts thereof which are preferred are also those in which one of the radicals X and Y is halogen, $(C_1-C_4)$alkyl, $(C_1-C_4)$alkoxy, $(C_1-C_4)$haloalkyl, $(C_1-C_4)$haloalkoxy or mono- or di[$(C_1-C_4)$alkyl]amino and the other of the radicals X and Y is $(C_1-C_4)$alkyl, $(C_1-C_4)$alkoxy or $(C_1-C_4)$ haloalkoxy.

Compounds (I) according to the invention and salts thereof which are preferred are also those in which the group of the formula $S(O)_n$—$R^1$ is in the 2-position and the group R*NH is in the 5-position relative to the sulfonylurea radical.

The present invention furthermore relates to processes for the preparation of the compounds of the formula (I) according to the invention or salts thereof, which comprise a) reacting a compound of the formula (II)

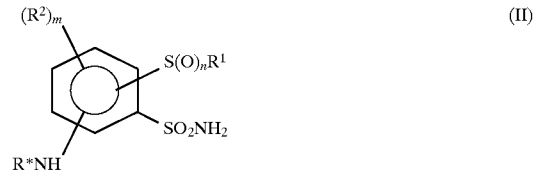

(II)

with a heterocyclic carbamate of the formula (III)

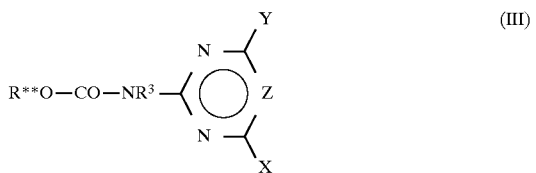

in which R** is unsubstituted or substituted phenyl or ($C_1$–$C_4$)alkyl, or b) reacting a sulfochloride of the formula (IV)

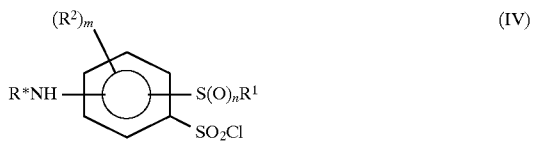

with a heterocyclic amine of the formula (V)

in the presence of a cyanate, for example an alkali metal cyanate, such as sodium cyanate or potassium cyanate, or c) reacting a sulfonamide of the formula (II) (cf. a) successively with a chloroformic acid aryl ester of the formula (VI)

Ar—O—CO—Cl         (VI)

in which Ar is an unsubstituted or substituted aryl radical, and with a heterocyclic amine of the formula (V) (cf. b), or d) formylating a sulfonylurea of the formula (VII)

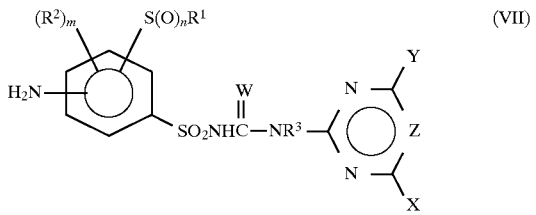

analogously to known methods to give the compound of the formula (I), in which
R*=CHO, and, in the case where R*=CH=NR or R=CH($X^1$R') ($X^2$R''), derivatizing the resulting formyl compound to give the formyl equivalent mentioned of the formula (I), or e) reacting a sulfonamide of the formula (II) (cf. variant a) with a (thio)isocyanate of the formula (VIII)

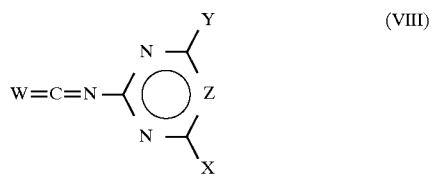

in the presence of a suitable base, where, in the above formulae (II) to (VIII), the radicals $R^1$, $R^2$, $R^3$, R*, W, X, Y and Z and the indices m and n are as defined in formula (I), and in variants a) to c), compounds of the formula (I) where W=O are first obtained.

The reaction of the compounds of the formulae (II) and (III) is preferably carried out under base catalysis in inert solvents, such as, for example, methylene chloride, acetonitrile, dioxane, dimethylformamide (DMF), dimethylacetamide or tetrahydrofuran (THF), at temperatures from −10° C. up to the boiling point of the particular solvent. Bases which are used here are, for example, organic amine bases, such as 1,8-diazabicyclo[5.4.0]undec-7-ene (DBU) or triethylamine, or else hydroxides, such as, for example, sodium hydroxide or potassium hydroxide, or alcoholates, such as, for example, sodium methylate, potassium tert-butylate or sodium phenolate, or carbonates, such as, for example, sodium carbonate or potassium carbonate, in particular in the case where R=(substituted) phenyl (cf., for example, EP-A-44807), or trimethyl- or triethylaluminum, the latter in particular in the case where R=alkyl (cf. EP-A-155516).

The sulfonamides of the formula (II) are obtainable, for example, by the following routes; cf. Equation 1, example for the preparation of compound (IIa)=(II) where R*=CHO:

The reaction of the sulfonic acids (IX) or alkali metal salts thereof with a chlorinating agent—such as, for example, $PCl_3$, $POCl_3$ or $SOCl_2$—leads to the sulfochloride of the formula (X). This reaction is carried out in bulk or in inert solvents, such as, for example, methylene chloride, sulfolane or acetonitrile or in a solvent mixture of inert components. The subsequent reaction with ammonia or tert-butylamine leads to the sulfonamides of the formula (XI) where R=H or tert-butyl. These compounds can be converted with mercaptans in solvents, such as, for example, dimethylformamide, N,N-dimethylacetamide or N-methylpyrrolidinone, in the presence of suitable bases, such as, for example, sodium carbonate or potassium carbonate, into the corresponding mercaptans of the formula (XII) (n=0). By the choice of suitable oxidizing agents (for example potassium peroxomonosulfate, ®Oxone) and reaction conditions, the corresponding compounds of the formula (XII) where n=1 and 2 can be prepared analogously to known methods.

After the reduction of the nitro group from the compounds of the formula (XII), for example with iron in an acetic acid medium or other customary methods (for example hydrogenation with Pd—C/hydrogen), the aniline of the formula (XIII) is obtained.

This compound is formylated by methods analogous to those known from the literature, for example with formic acid and acetic anhydride, to give the compounds of the formula (IIa) or (XIV). In the case where R=tert-butyl, the tert-butyl group is split off from the aromatics of the formula (XIV) by reaction with strong acids to give the sulfonamides of the formula (IIa). Possible strong acids are, for example, mineral acid, such as, for example, $H_2SO_4$ or HCl, or strong organic acids, such as, for example, $CF_3COOH$.

Equation 1: Synthesis of the sulfonamides (IIa)

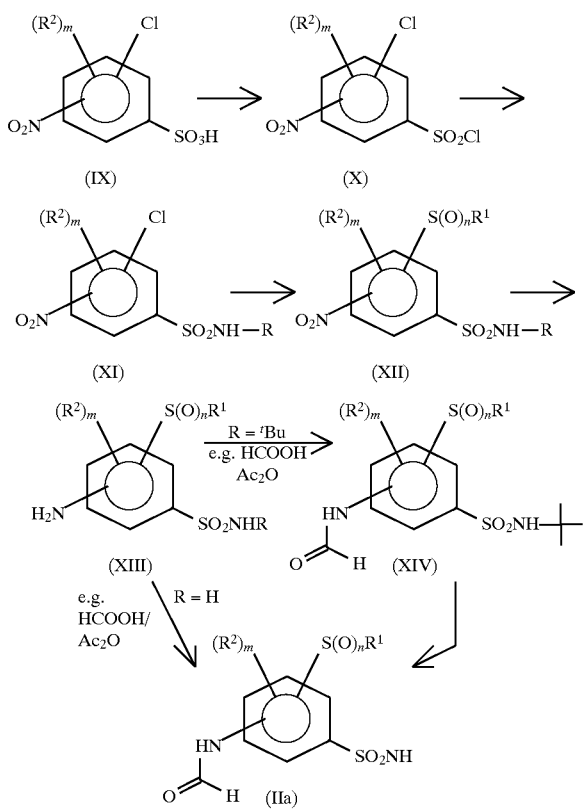

Derivatization of the compounds (IIa) on the formyl group to give other groups such as occur in formula (I) can be carried out at this stage analogously to known processes.

The carbamates of the formula (III) required for the reaction of the compounds (II) by variant a) are known from the literature or can be prepared analogously to known processes (cf. EP-A-70804 or U.S. Pat. No. 4,480,101).

For compounds of the formula (I) where n=2 and $R^1$=the nitrogen or oxygen function, another synthesis route is recommended as an alternative to Equation 1. Compounds of the formula (XII) where n=0 and, for example, $R^1$=benzyl are converted into the corresponding sulfochlorides of the formula (XV) by oxidative chlorination with chlorine or hypochlorite. The nitroaromatics of the formula (XII) (n=2, $R^1$=O—R', $R^1$=NR"R"') are obtainable by reaction of alcoholates, phenolates or a with the sulfochloride of the formula (XV). The further synthesis sequence to give the corresponding sulfonylureas of the formula (I) (n=2, $R^1$=OR', $R^1$=NR"R"') can be carried out analogously to the transformation of compound (XII)→compound (I) described above (cf. Equation 2).

Equation 2:

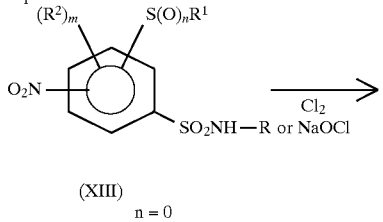

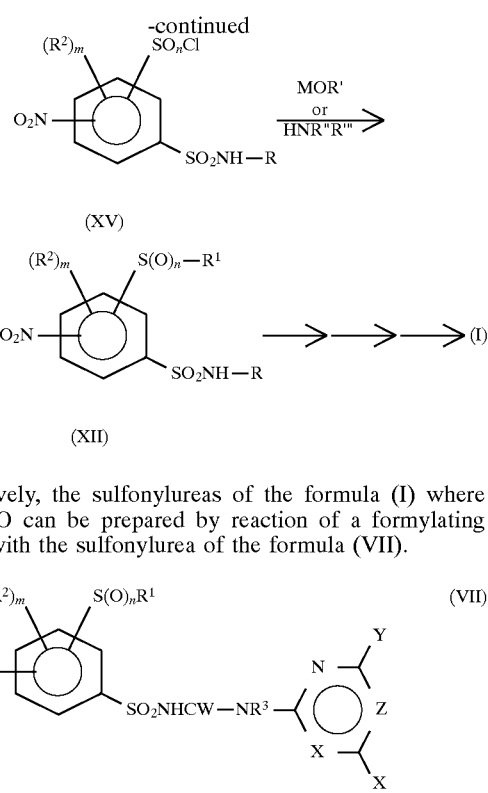

Alternatively, the sulfonylureas of the formula (I) where $R^*$=CHO can be prepared by reaction of a formylating reagent with the sulfonylurea of the formula (VII).

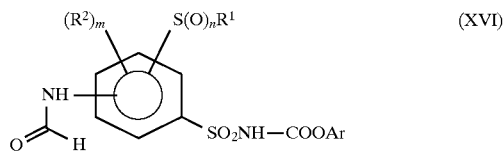

For this, the compounds of the formula (VII) are initially introduced into the reaction vessel at temperatures between −10° C. and 70° C., preferably 0° to 40° C., in an inert solvent, such as, for example, methylene chloride, chloroform, dimethylformamide or N,N-dimethylacetamide, and a suitable formylating agent, for example the mixed anhydride of formic and acetic acid, is added. Compounds of the formula (VII) are known from the literature (EP-A-23141, U.S. Pat. No. 4,369,058) or can be prepared in a manner analogous to the processes described therein.

The reactions of sulfonamides of the formula (II) with chloroformic acid aryl esters (VI) and heterocyclic amines of the formula (V) likewise lead to the compounds of the formula (I). From the sulfonamides of the formula (IIa) and chloroformic acid aryl esters (for example Ar=phenyl), the corresponding sulfonylcarbamates of the formula (XVI)

are first formed in the presence of a suitable base, such as, for example, triethylamine or potassium carbonate. These sulfonylcarbamates of the formula (XVI) can then be reacted with heterocyclic amines (V) to give the sulfonylureas (I) (cf. U.S. Pat. No. 4,994,571).

The reaction of the sulfochlorides (IV) with the amino-heterocyclic compounds of the formula (V) and cyanates, such as sodium cyanate and potassium cyanate, is carried out, for example, in aprotic solvents, such as, for example, acetonitrile, sulfolane, N-methylpyrrolidone, dimethylformamide, pyridine, picoline or lutidine, or a mixture of the solvents mentioned, at temperatures between −10° C. and 100° C., preferably between 0° and 50° C. (cf. U.S. Pat. No. 5,157,119).

The (thio)isocyanates of the formula (VIII) are obtainable by processes known from the literature (EP-A-232067, EP-A-166516). The reaction of the (thio)isocyanates (VIII) with compounds (II) is carried out at −10° C. to 100° C., preferably 20° to 100° C., in an inert aprotic solvent, such as, for example, acetone or acetonitrile, in the presence of a suitable base, for example $N(C_2H_5)_3$ or $K_2CO_3$.

The salts of the compounds of the formula (I) are preferably prepared in inert polar solvents, such as, for example, water, methanol, acetone, methylene chloride or tetrahydrofuran, and in individual cases also in non-polar solvents, such as toluene or heptane, at temperatures from 0° to 100° C. Suitable bases for preparation of the salts according to the invention are, for example, alkali metal carbonates, such as sodium carbonate, alkali metal and alkaline earth metal hydroxides, for example NaOH, KOH or $Ca(OH)_2$, ammonia or a suitable amine base from the group consisting of primary, secondary and tertiary amines, such as triethylamine or ethanolamine. Suitable acids for the salt formation are, for example, HCl, HBr, $H_2SO_4$ or $HNO_3$.

The intermediates of the formulae (II), (IV), (XIV) and (XVI) are novel and the present invention likewise relates to these; together, they correspond to compounds of the formula (XVII)

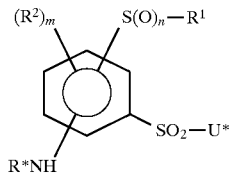

in which U* is $NH_2$, Cl or mono- or disubstituted amino, such as alkylamino, in particular t-butylamino, or aryloxycarbonylamino, and R*, $R^1$, $R^2$, n and m are defined as in formula (I).

The "inert solvents" mentioned in the above process variants mean in each case solvents which are inert under the particular reaction conditions but which do not have to be inert under any desired reaction conditions.

The term "compounds of the formula (I) according to the invention" below summarily also relates to salts of the compounds of the formula (I).

The compounds of the formula (I) according to the invention have an excellent herbicidal activity against a broad spectrum of economically important mono- and dicotyledon harmful plants. Perennial weeds which are difficult to control and shoot from rhizomes, rootstock or other permanent organisms are also readily attacked by the active compounds. It is irrelevant here whether the substances are applied prior to sowing, pre-emergence or post-emergence.

Some representatives of monocotyledon and dicotyledon weed flora which can be controlled by the compounds according to the invention may be mentioned specifically by way of example, without a limitation to certain species being intended by the naming of these.

On the part of the monocotyledon species of weeds, for example, Avena, Lolium, Alopecurus, Phalaris, Echinochloa, Digitaria, Setaria and Cyperus species from the annual group and on the part of the perennial species, Agropyron, Cynodon, Imperata and Sorghum and also perennial Cyperus species are readily attacked.

In the case of dicotyledon species of weeds, the action spectrum extends to species such as, for example, Galium, Viola, Veronica, Lamium, Stellaria, Amaranthus, Sinapis, Ipomoea, Matricaria, Abutilon and Sida on the annual side, and Convolvulus, Cirsium, Rumex and Artemisia in the case of perennial weeds.

Weeds which occur under the specific growing conditions in rice, such as, for example, Sagittaria, Alisma, Eleocharis, Scirpus and Cyperus, are likewise controlled outstandingly by the active compounds according to the invention.

If the compounds according to the invention are applied to the soil surface before germination, either the emergence of the weed seedlings is prevented completely or the weeds grow to the cotyledon stage but then stop their growth and finally die completely at the end of three to four weeks.

If the active compounds are applied to the green parts of plants by the post-emergence method, a drastic stop in growth likewise occurs very rapidly after the treatment and the weed plants remain in the growth stage existing at the time of application or die completely after a certain period of time, so that weed competition, which is harmful to the crop plants, is eliminated very early and lastingly in this manner.

Although the compounds according to the invention have an excellent herbicidal activity against monocotyledon and dicotyledon weeds, crop plants of economically important crops, such as, for example, wheat, barley, rye, rice, maize, sugar beet, cotton and soya, are harmed only insignificantly or not at all. For these reasons, the present compounds are particularly suitable for selective control of undesirable plant growth in agricultural crop plantations.

The substances according to the invention furthermore have outstanding growth regulatory properties in crop plants. They intervene in the endogenous metabolism of the plants in a regulating manner and can therefore be employed for controlled influencing of plant contents and for facilitating harvesting, such as, for example, by inducing desiccation and stunted growth. They are furthermore also suitable for general control and inhibition of undesirable vegetative growth without killing the plants at the same time. Inhibition of vegetative growth plays a major rôle in many monocotyledon and dicotyledon crops, since lodging can be reduced or prevented completely by this means.

The compounds according to the invention can be used in the customary formulations in the form of wettable powders, emulsifiable concentrates, sprayable solutions, dusting powders or granules. The invention therefore also relates to herbicidal and plant growth-regulating compositions which comprise the compounds of the formula (I).

The compounds of the formula (I) can be formulated in various ways, depending on the biological and/or chemico-physical parameters which exist. Suitable formulation possibilities are, for example: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil- or water-based dispersions, oil-miscible solutions, capsule suspensions (CS), dusting powders (DP), seed dressings, granules for application by scattering and to the soil, granules (GR) in the form of microgranules, sprayed granules, absorption granules and adsorption granules, water-dispersible granules (WG), water-soluble granules (SG), ULV formulations, microcapsules and waxes.

These individual types of formulation are known in principle and are described, for example, in: Winnacker-Küchler, "Chemische Technologie" [Chemical technology], Volume 7, C. Hauser Verlag Munich, 4th edition 1986, Wade van Valkenburg, "Pesticide Formulations", Marcel Dekker, N.Y., 1973; K. Martens, "Spray Drying", Handbook, 3rd edition 1979, G. Goodwin Ltd. London.

The necessary formulating auxiliaries, such as inert materials, surfactants, solvents and further additives, are likewise known and are described, for example, in: Watkins, "Handbook of Insecticide Dust Diluents and Carriers", 2nd edition, Darland Books, Caldwell, N.J., H.v. Olphen, "Introduction to Clay Colloid Chemistry"; 2nd edition, J. Wiley & Sons, N.Y.; C. Marsden, "Solvents Guide"; 2nd edition, Interscience, N.Y. 1963; McCutcheon's "Detergents and Emulsifiers Annual", MC Publ. Corp., Ridgewood, N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active ethylene oxide adducts], Wiss. Verlagsgesell., Stuttgart 1976; Winnacker-Küchler, "Chemische Technologie" [Chemical technology], Volume 7, C. Hauser Verlag Munich, 4th edition 1986.

Combinations with other substances having a pesticidal action, such as, for example, insecticides, acaricides, herbicides and fungicides, and with safeners, fertilizers and/or growth regulators, can be prepared on the basis of these formulations, for example in the form of a ready-to-use formulation or as a tank mix.

Wettable powders are preparations which are uniformly dispersible in water and which, alongside the active compound, and in addition to a diluent or inert substance, also comprise surfactants of an ionic and/or nonionic nature (wetting agents, dispersing agents), for example polyoxyethylated alkylphenols, polyoxyethylated fatty alcohols, polyoxyethylated fatty amines, fatty alcohol polyglycol ether-sulfates, alkanesulfonates, alkylbenzenesulfonates, sodium ligninsulfonate, sodium 2,2'-dinaphthylmethane-6,6'-disulfonate, sodium dibutylnaphthalene-sulfonate or sodium oleylmethyltauride. To prepare the wettable powders, for example, the herbicidal active compounds are finely ground in customary apparatuses, such as hammer mills, blast mills and air jet mills, and are mixed with the formulating auxiliaries at the same time or subsequently.

Emulsifiable concentrates are prepared by dissolving the active compound in an organic solvent, for example butanol, cyclohexanone, dimethylformamide, xylene or also higher-boiling aromatics or hydrocarbons or mixtures of organic solvents, with the addition of one or more surfactants of an ionic and/or nonionic nature (emulsifiers). Emulsifiers which can be used are, for example: calcium alkylarylsulfonates, such as Ca dodecylbenzenesulfonate, or nonionic emulsifiers, such as fatty acid polyglycol esters, alkylarylpolyglycol ethers, fatty alcohol polyglycol ethers, propylene oxide/ethylene oxide condensation products, alkyl polyethers, sorbitan esters, such as, for example, sorbitan fatty acid esters, or polyoxyethylene sorbitan esters, such as, for example, polyoxyethylene sorbitan fatty acid esters.

Dusting powders are obtained by grinding the active compound with finely divided solid substances, for example talc, naturally occurring clays, such as kaolin, bentonite and pyrophyllite, or diatomaceous earth.

Suspension concentrates can be water- or oil-based. They can be prepared, for example, by wet grinding by means of commercially available bead mills and, if appropriate, with the addition of surfactants, such as are already listed above, for example, for the other types of formulation.

Emulsions, for example oil-in-water emulsions (EW), can be prepared, for example, by means of stirrers, colloid mills and/or static mixers using aqueous organic solvents and if appropriate surfactants, such as are already listed above, for example, for the other types of formulation.

Granules can be prepared either by spraying the active compound onto granular inert material capable of adsorption or by applying active compound concentrates to the surface of carrier substances, such as sand, kaolinites or granular inert material, by means of adhesives, for example polyvinyl alcohol, sodium polyacrylate or mineral oils. Suitable active compounds can also be granulated in the manner customary for the preparation of fertilizer granules—if desired as a mixture with fertilizers.

Water-dispersible granules are as a rule prepared by customary processes, such as spray drying, fluidized bed granulation, disk granulation, mixing with high-speed mixers and extrusion, without a solid inert material. For the preparation of disk, fluidized bed, extruder and sprayed granules cf., for example, processes in "Spray-drying Handbook" 3rd edition 1979. G. Goodwin Ltd., London; J. E. Browning, "Agglomeration", Chemical and Engineering 1967, pages 147 et seq.; "Perry's Chemical Engineer's Handbook", 5th edition, McGraw-Hill, New York 1973, pages 8–57.

For further details on the formulation of plant protection agents cf., for example, G. C. Klingman, "Weed Control as a Science", John Wiley and Sons, Inc., New York, 1961, pages 81–96 and J. D. Freyer, S. A. Evans, "Weed Control Handbook", 5th edition, Blackwell Scientific Publications, Oxford, 1968, pages 101–103.

The agrochemical formulations as a rule comprise 0.1 to 99% by weight, in particular 0.1 to 95% by weight, of active compound of the formula (I). In wettable powders, the active compound concentration is, for example, about 10 to 90% by weight, the remainder to make up 100% by weight comprising customary formulation constituents. In emulsifiable concentrates, the active compound concentration can be about 1 to 90, preferably 5 to 80% by weight. Dust-like formulations comprise 1 to 30% by weight of active compound, preferably usually 5 to 20% by weight of active compound, and sprayable solutions comprise about 0.05 to 80, preferably 2 to 50% by weight of active compound. In water-dispersible granules, the active compound content partly depends on whether the active compound is present in liquid or solid form and what granulating auxiliaries, fillers and the like are used. In water-dispersible granules, the content of active compound is, for example, between 1 and 95% by weight, preferably between 10 and 80% by weight.

In addition, the active compound formulations mentioned comprise, if appropriate, the particular customary tackifiers, wetting agents, dispersing agents, emulsifiers, penetration agents, preservatives, antifreezes and solvents, fillers, carrier substances and dyestuffs, defoamers, evaporation inhibitors and agents which influence the pH and viscosity.

Known active compounds such as are described, for example, in Weed Research 26, 441–445 (1986), or "The Pesticide Manual", 9th edition, The British Crop Protection Council, 1990/91, Bracknell, England, and literature mentioned therein can be employed as combination partners for the active compounds according to the invention in mixture formulations or in a tank mix. The following active compounds may be mentioned, for example, as herbicides which are known from the literature and can be combined with the compounds of the formula (I) (Note: The compounds are named either with the "common name" according to the International Organization for Standardization (ISO) or with the chemical name, if appropriate together with a customary code number):

acetochlor; acifluorfen; aclonifen; AKH 7088, i.e. [[[1-[5-[2-chloro-4-(trifluoromethyl)phenoxy]-2-nitrophenyl]-2-methoxyethylidene]amino]oxy]acetic acid and -acetic acid methyl ester; alachlor; alloxydim; ametryn; amidosulfuron; amitrol; AMS, i.e. ammonium sulfamate; anilofos; asulam; atrazin; azimsulfurone (DPX-A8947); aziprotryn; barban; BAS 516 H, i.e. 5-fluoro-2-phenyl-4H-3,1-benzoxazin-4-one; benazolin; benfluralin; benfuresate; bensulfuron-methyl; bensulide; bentazone; benzofenap; benzofluor; benzoyl-prop-ethyl; benzthiazuron; bialaphos; bifenox; bromacil; bromobutide; bromofenoxim; bromoxynil; bromuron; buminafos; busoxinone; butachlor; butamifos; butenachlor; buthidazole; butralin; butylate; cafenstrole (CH-900); carbetamide; cafentrazone (ICI-A0051); CDAA, i.e. 2-chloro-N,N-di-2-propenylacetamid; CDEC, i.e. diethyl-dithiocarbamic acid 2-chloroallyl ester; chlomethoxyfen; chloramben; chlorazifop-butyl, chlormesulon (ICI-A0051); chlorbromuron; chlorbufam; chlorfenac; chlorflurecol-methyl; chloridazon; chlorimuron ethyl; chlornitrofen; chlorotoluron; chloroxuron; chlorpropham; chlorsulfuron; chlorthal-dimethyl; chlorthiamid; cinmethylin; cinosulfuron; clethodim; clodinafop and ester derivatives thereof (for example clodinafop-propargyl); clomazone; clomeprop; cloproxydim; clopyralid; cumyluron (JC 940); cyanazine; cycloate; cyclosulfamuron (AC 104); cycloxydim; cycluron; cyhalofop and ester derivatives thereof (for example butyl ester, DEH-112); cyperquat; cyprazine; cyprazole; daimuron; 2,4-DB; dalapon; desmedipham; desmetryn; di-allate; dicamba; dichlobenil; dichlorprop; diclofop and esters thereof, such as diclofop-methyl; diethatyl; difenoxuron; difenzoquat; diflufenican; dimefuron; dimethachlor; dimethametryn; dimethenamid (SAN-582H); dimethazone, clomazon; dimethipin; dimetrasulfuron, dinitramine; dinoseb; dinoterb; diphenamid; dipropetryn; diquat; dithiopyr; diuron; DNOC; eglinazine-ethyl; EL 177, i.e. 5-cyano-1-(1,1-dimethylethyl)-N-methyl-1H-pyrazole-4-carboxamide; endothal; EPTC; esprocarb; ethalfluralin; ethametsulfuron-methyl; ethidimuron; ethiozin; ethofumesate; F5231, i.e. N-[2-chloro-4-fluoro-5-[4-(3-fluoropropyl)-4,5-dihydro-5-oxo-1H-tetrazol-1-yl]-phenyl]ethanesulfonamide; ethoxyfen and esters thereof (for example ethyl ester, HN-252); etobenzanid (HW 52); fenoprop; fenoxan, fenoxaprop and fenoxaprop-P and esters thereof, for example fenoxaprop-P-ethyl and fenoxaprop-ethyl; fenoxydim; fenuron; flamprop-methyl; flaza-sulfuron; fluazifop and fluazifop-P and esters thereof, for example fluazifop-butyl and fluazifop-P-butyl; fluchloralin; flumetsulam; flumeturon; flumiclorac and esters thereof (for example pentyl ester, S-23031); flumioxazin (S-482); flumipropyn; flupoxam (KNW-739); fluorodifen; fluoroglycofen-ethyl; flupropacil (UBIC-4243); fluridone; flurochloridone; fluroxypyr; flurtamone; fomesafen; fosamine; furyloxyfen; glufosinate; glyphosate; halosaten; halosulfuron and esters thereof (for example methyl ester, NC-319); haloxyfop and esters thereof; haloxyfop-P (=R-haloxyfop) and esters thereof; hexazinone; imazamethabenz-methyl; imazapyr; imazaquin and salts, such as the ammonium salt; imazethamethapyr; imazethapyr; imazosulfuron; ioxynil; isocarbamid; isopropalin; isoproturon; isouron; isoxaben; isoxapyrifop; karbutilate; lactofen; lenacil; linuron; MCPA; MCPB; mecoprop; mefenacet; mefluidid; metamitron; metazachlor; methabenzthiazuron; metham; methazole; methoxyphenone; methyldymron; metabenzuron, methobenzuron; metobromuron; metolachlor; metosulam (XRD 511); metoxuron; metribuzin; metsulfuron-methyl; MH; molinate; monalide; monocarbamide dihydrogensulfate; monolinuron; monuron; MT 128, i.e. 6-chloro-N-(3-chloro-2-propenyl)-5-methyl-N-phenyl-3-pyridazinamine; MT 5950, i.e. N-[3-chloro-4-(1-methylethyl)phenyl]-2-methylpentanamide; naproanilide; napropamide; naptalam; NC 310, i.e. 4-(2,4-dichlorobenzoyl)-1-methyl-5-benzyloxypyrazole; neburon; nicosulfuron; nipyraclophen; nitralin; nitrofen; nitrofluorfen; norflurazon; orbencarb; oryzalin; oxa-diargyl (RP-020630); oxadiazon; oxyfluorfen; paraquat; pebulate; pendimethalin; perfluidone; phenisopham; phenmedipham; picloram; piperophos; piributicarb; pirifenopbutyl; pretilachlor; primisulfuron-methyl; procyazine; prodiamine; profluralin; proglinazine-ethyl; prometon; prometryn; propachlor; propanil; propaquizafop and esters thereof; propazine; propham; propisochlor; propyzamide; prosulfalin; prosulfocarb; prosulfuron (CGA-152005); prynachlor; pyrazolinate; pyrazon; pyrazosulfuron-ethyl; pyrazoxyfen; pyridate; pyrithiobac (KIH-2031); pyroxofop and esters thereof (for example propargyl ester); quinclorac; quinmerac; quinofop and ester derivatives thereof, quizalofop and quizalofop-P and ester derivatives thereof, for example quizalofop-ethyl; quizalofop-P-tefuryl and -ethyl; renriduron; rimsulfuron (DPX-E-9636); S 275, i.e. 2-[4-chloro-2-fluoro-5-(2-propynyloxy)phenyl]-4,5,6,7-tetrahydro-2H-indazole; secbumeton; sethoxydim; siduron; simazine; simetryn; SN 106279, i.e. 2-[[7-[2-chloro-4-(trifluoromethyl)-phenoxy]-2-naphthalenyl]oxy]propanoic acid and its methyl ester; sulfentrazon (FMC-97285, F-6285); sulfazuron; sulfometuron-methyl; sulfosate (ICI-A0224); TCA; tebutam (GCP-5544); tebuthiuron; terbacil; terbucarb; terbuchlor; terbumeton; terbuthylazine; terbutryn; THF 450, i.e. N,N-diethyl-3-[(2-ethyl-6-methylphenyl)sulfonyl]-1H-1,2,4-triazole-1-carboxamide; thenylchlor (NSK-850); thiazafluoron; thizopyr (Mon-13200); thidiazimin (SN-124085); thifensulfuronmethyl; thiobencarb; tiocarbazil; tralkoxydim; triallate; triasulfuron; triazofenamide; tribenuron-methyl; triclopyr; tridiphane; trietazine; trifluralin; triflusulfuron and esters (for example methyl ester, DPX-66037); trimeturon; tsitodef; vernolate; WL 110547, i.e. 5-phenoxy-1-[3-(trifluoromethyl)phenyl]-1H-tetrazole; UBH-509; D-489; LS 82-556; KPP-300; NC-324; NC-330; KH-218; DPX-N8189; SC-0774; DOWCO-535; DK-8910; V-53482; PP-600; MBH-001; KIH-9201; ET-751; KIH-6127 and KIH-2023.

For use, the formulations in the commercially available form are diluted in the customary manner, if appropriate, for example by means of water in the case of wettable powders, emulsifiable concentrates, dispersions and water-dispersible granules. Dust-like formulations, soil or scattering granules and sprayable solutions are usually not diluted further with additional inert substances before use.

The required amount of compounds of the formula (I) to be applied varies with the outdoor conditions, such as temperature and humidity, the nature of the herbicide used and the like. It can vary within wide limits, for example between 0.001 and 10.0 kg/ha or more of active substance, but is preferably between 0.005 and 5 kg/ha.

CHEMICAL EXAMPLES a) N-tert-Butyl-2-chloro-5-nitrobenzenesulfonamide 165 g of dried 2-chloro-5-nitrobenzenesulfonic acid sodium salt (90% pure) are initially introduced into 264 ml of acetonitrile, 264 ml of sulfolane and 16.5 ml of dimethylformamide (DMF). After dropwise addition of 198 ml of phosphorus oxychloride, the mixture is heated at the boiling point for 2 hours. After the mixture has been cooled, it is poured onto cold water and extracted with ethyl acetate, and the combined organic phases are dried over sodium sulfate and concentrated. The residue (mixture of sulfolane and 2-chloro-5-nitrobenzenesulfonyl chloride) is taken up in 1500 ml of methylene chloride, 130 ml of tert-butylamine are added (ice-bath cooling) and the mixture is stirred at room temperature for about 2 hours. After washing with dilute hydrochloric acid and drying over $MgSO_4$, the organic phase is concentrated. The residue is stirred with methanol and cooled to 0° C. The solid which has separated out (109 g, melting point 168° to 171° C.) is separated off and dried. A second fraction of the product of comparable quality (46.7 g) can be isolated analogously from the mother liquor.

b) N-tert-Butyl-2-ethylmercapto-5-nitrobenzene-sulfonamide 5.6 ml of ethylmercaptan are added to a suspension of 20.0 g of N-tert-butyl-2-chloro-5-nitrobenzenesulfonamide, 18.9 g of potassium carbonate and 100 ml of DMF at room temperature. After the mixture has been stirred for 3 hours, it is concentrated under a high vacuum. The residue is taken up in water and acidified with concentrated hydrochloric acid (pH 1 to 2). The aqueous phase is extracted with ethyl acetate. The combined organic phases are dried over magnesium sulfate and then concentrated under reduced pressure. 21.25 g of the desired ethylmercaptan are thus obtained; melting point: 172° to 174° C.

c) 5-Amino-2-ethylmercapto-N-tert-butylbenzene-sulfonamide 13.3 g of zinc powder are added in portions to a mixture of 12 g of N-tert-butyl-2-ethylmercapto-5-nitrobenzenesulfonamide, 17.7 g of ammonium chloride, 50 ml of water and 200 ml of ethanol and the mixture is stirred at 70° C. for 10 hours. After the solid has been filtered off and washed out with ethyl acetate, the filtrate is concentrated under reduced pressure. The residue from the filtrate is taken up in ethyl acetate and the mixture is washed with water. After drying over magnesium sulfate, the organic phase is concentrated. 9.4 g of the desired aniline are thus obtained;

$^1$H-NMR (80 MHz, D$^6$-DMSO): δ ppm=1.10 (s, 9H, C(C$\underline{H}_3$)$_3$); 1.15 (t, 2H, CH$_2$C$\underline{H}_3$); 2.85 (q, 2H, C$\underline{H}_2$CH$_3$); 5.60 (s, 2H, N$\underline{H}_2$); 6.60 (s, 1H, N$\underline{H}$); 6.70 (dd, 1H, 4-H); 7.20 (d, 1H, 6-H); 7.30 (d, 1H, 3-H).

d) N-tert-Butyl-2-ethylmercapto-5-formylaminobenzo-sulfonamide 1.1 ml of formic acid are added dropwise to 2.5 ml of acetic anhydride. After the mixture has been heated at 50° C. for 1 hour, the solution is cooled to room temperature and 3.0 g of 5-amino-2-ethylmercapto-N-tert-butyl-benzenesulfonamide, dissolved in 10 ml of DMF, are added. After the reaction mixture has been stirred at 50° C. for 1 hour it is concentrated under a high vacuum. The residue is taken up in ethyl acetate and the mixture is washed with dilute hydrochloric acid and water. After drying over magnesium sulfate, the organic phase is concentrated. 3.13 g of the desired formylaniline derivative, which can be employed for further reactions without further purification, are thus obtained.

e) 2-Ethylmercapto-5-formylaminobenzenesulfonamide 3.13 g of N-tert-butyl-2-ethylmercapto-5-formylaminobenzenesulfonamide are stirred in 20 ml of trifluoroacetic acid at room temperature. When the reaction has ended, volatile components are distilled off under a high vacuum. 3.20 g of a solid which has an adequate purity for further reactions are thus obtained; melting point: 127° C.

f) N-[(4,6-Dimethoxypyrimidin-2-yl)aminocarbonyl]-2-ethylmercapto-5-formylaminobenzenesulfonamide (Table 1, Example 1-26)

3.4 ml of DBU are added dropwise to a suspension of 3.0 g of 2-ethylmercapto-5-formylaminobenzenesulfonamide and 4.6 g of 4,6-dimethoxy-2-phenoxycarbonylamino-pyrimidine in 30 ml of acetonitrile at 0° C. When the reaction has ended, the acetonitrile is distilled off, the residue is taken up in water and the mixture is washed with diethyl ether. After the aqueous phase has been acidified with concentrated hydrochloric acid (pH=1 to 2), the solid which has precipitated out is separated off and washed with diisopropyl ether. 1.13 g of the desired sulfonylurea which has an adequate purity for biological experiments are thus obtained; melting point: 185° to 187° C. (with decomposition).

g) N-tert-Butyl-2-ethylsulfonyl-5-nitrobenzenesulfonamide

A solution of 180 g of ®Oxone (potassium peroxomonosulfate) in 600 ml of water is added dropwise to a solution of 60.0 g of N-tert-butyl-2-ethylmercapto-5-nitrobenzenesulfonamide in 900 ml of methanol at a temperature of 65° C. After the reaction mixture has been stirred at this temperature for 5 hours it is cooled, poured onto water and extracted with ethyl acetate. The combined organic phases are washed with water, dried over magnesium sulfate and then concentrated. 60.6 g of the ethyl sulfone are thus obtained; melting point: 108° to 111° C.

h) 5-Amino-N-tert-butyl-2-ethylsulfonylbenzene-sulfonamide

A mixture of 40 g of N-tert-butyl-2-ethylsulfonyl-5-nitrobenzenesulfonamide is dissolved in 1500 ml of methanol, 0.5 g of 10% palladium on charcoal is added and the mixture is stirred under a hydrogen atmosphere (1 atmosphere). When the uptake of hydrogen has ended, the catalyst is separated off and the solution is concentrated. 32.9 g of the aniline derivative are thus obtained;

melting point: 193° to 195° C.

i) N-tert-Butyl-2-ethylsulfonyl-5-formylaminobenzene-sulfonamide 0.82 ml of formic acid is added dropwise to 1.85 ml of acetic anhydride. After the mixture has been stirred at 50° C. for 2 hours, a solution of 2.5 g of 5-amino-N-tert-butyl-2-ethylsulfonylbenzenesulfonamide in 10 ml of DMF is added dropwise at room temperature. This mixture is first stirred at 50° C. for 3 hours and then concentrated under a high vacuum. The residue is taken up in water and the mixture is extracted with ethyl acetate. After the organic phase been dried over magnesium sulfate, the solvent is distilled off. The residue (3.0 g) contains the desired product and is of adequate purity for further reactions.

j) 2-Ethylsulfonyl-5-formylaminobenzenesulfonamide 3.0 g of N-tert-butyl-2-ethylsulfonyl-5-formylaminobenzenesulfonamide are stirred in 20 ml of trifluoroacetic acid. When the reaction has ended, the trifluoroacetic acid is distilled off. The residue is stirred with a little ethyl acetate. After the solid has been separated off and dried, 1.65 g of the desired sulfonamide are obtained; melting point: 186° to 189° C.

k) N-[(4,6-Dimethoxypyrimidin-2-yl)aminocarbonyl]-2-ethylsulfonyl-5-formylaminobenzenesulfonamide (Table 3, Example 3-26)

0.86 ml of DBU is added dropwise to a suspension of 1.30 g of 2-ethylsulfonyl-5-formylaminobenzenesulfonamide and 1.50 g of 4,6-dimethoxy-2-phenoxycarbonylamino-pyrimidine in 40 ml of acetonitrile. The mixture is then subsequently stirred at room temperature. When the reaction has ended, acetonitrile is distilled off. The residue is taken up in water and the mixture is washed with diethyl ether. The aqueous phase is acidified with concentrated hydrochloric acid (pH=1 to 2). The solid which has separated out is washed with diisopropyl ether and then dried. 1.65 g of the desired sulfonylurea are thus obtained; melting point: from 152° C. with decomposition.

1) N-[(4,6-Dimethoxypyrimidin-2-yl)aminocarbonyl]-2-ethylsulfonyl-5-formylaminobenzenesulfonamide sodium salt (Table 3, Example 3-28)

10.0 g of N-[(4,6-dimethoxypyrimidin-2-yl)aminocarbonyl]-2-ethylsulfonyl-5-formylaminobenzenesulfonamide (cf. Example k) are initially introduced into 20 ml of methanol. After addition of 4.2 ml of a 30% strength solution of sodium methylate in methanol, the mixture is stirred at room temperature. After the solvent has been distilled off, 9.7 g of a colorless solid which has an adequate purity for the subsequent biological experiments are obtained; melting point: from 197°–202° C. (decomposition).

The compounds described in the following Tables 1, 2, 3, 4, 5, 6 and 7 are obtained in accordance with or analogously to the above Examples a) to 1).

Abbreviations in the tables m.p.=solidification point in °C.=melting point in °C.
(d)=melting point with decomposition
Et=ethyl
Me=methyl
Pr=$^n$Pr=n-propyl
$^i$Pr=isopropyl
$^c$Pr=cyclopropyl
Bu=$^n$Bu=n-butyl
$^i$Bu=isobutyl
$^t$Bu=t-butyl
Ph=phenyl
$(R^2)_m$=Description of all the radicals $R^2$; in this column "-" means no substituent (m=0) and, for example, 4-Cl="Cl in the 4-position" (m=1)

TABLE 1

Compounds of the formula (Ia)

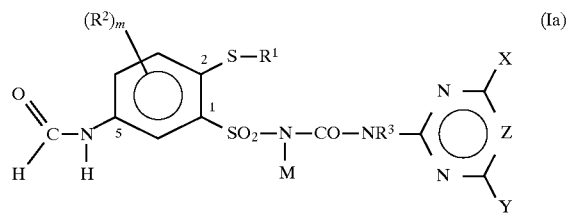

| Example number | R¹ | $(R^2)_m$ | R³ | M | X | Y | Z | m.p. |
|---|---|---|---|---|---|---|---|---|
| 1-1 | Me | — | H | H | OMe | OMe | CH | |
| 1-2 | Me | — | H | H | OMe | OMe | N | |
| 1-3 | Me | — | H | Na | OMe | OMe | CH | |
| 1-4 | Me | — | H | K | OMe | OMe | CH | |
| 1-5 | Me | — | H | NH₄ | OMe | OMe | CH | |
| 1-6 | Me | — | H | NMe₄ | OMe | OMe | CH | |
| 1-7 | Me | — | H | Na | OMe | OMe | N | |
| 1-8 | Me | — | H | K | OMe | OMe | N | |
| 1-9 | Me | — | H | NH₄ | OMe | OMe | N | |
| 1-10 | Me | — | H | H | OMe | Me | CH | |
| 1-11 | Me | — | H | Na | OMe | Me | CH | |
| 1-12 | Me | — | H | K | OMe | Me | CH | |
| 1-13 | Me | — | H | H | OMe | Me | N | |
| 1-14 | Me | — | H | Na | OMe | Me | N | |
| 1-15 | Me | — | H | K | OMe | Me | N | |
| 1-16 | Me | — | H | H | OMe | Cl | CH | |
| 1-17 | Me | — | H | Na | OMe | Cl | CH | |
| 1-18 | Me | — | H | K | OMe | Cl | CH | |
| 1-19 | Me | — | H | NH₄ | OMe | Cl | CH | |
| 1-20 | Me | — | H | H | Me | Me | CH | |
| 1-21 | Me | — | H | Na | Me | Me | CH | |
| 1-22 | Me | — | H | H | OCH₂CF₃ | NMe₂ | N | |
| 1-23 | Me | — | H | Na | OCH₂CF₃ | NMe₂ | N | |
| 1-24 | Me | — | H | H | OMe | SMe | N | |
| 1-25 | Me | — | H | H | SMe | SMe | N | |
| 1-26 | Et | — | H | H | OMe | OMe | CH | 185–7 (d) |
| 1-27 | Et | — | H | H | OMe | OMe | N | |
| 1-28 | Et | — | H | Na | OMe | OMe | CH | |
| 1-29 | Et | — | H | K | OMe | OMe | CH | |
| 1-30 | Et | — | H | NH₄ | OMe | OMe | CH | |
| 1-31 | Et | — | H | NMe₄ | OMe | OMe | CH | |
| 1-32 | Et | — | H | Na | OMe | OMe | N | |
| 1-33 | Et | — | H | K | OMe | OMe | N | |
| 1-34 | Et | — | H | NH₄ | OMe | OMe | N | |
| 1-35 | Et | — | H | H | OMe | Me | CH | |
| 1-36 | Et | — | H | Na | OMe | Me | CH | |
| 1-37 | Et | — | H | K | OMe | Me | CH | |
| 1-38 | Et | — | H | H | OMe | Me | N | |

TABLE 1-continued

Compounds of the formula (Ia)

| Example number | R¹ | (R²)ₘ | R³ | M | X | Y | Z | m.p. |
|---|---|---|---|---|---|---|---|---|
| 1-39 | Et | — | H | Na | OMe | Me | N | |
| 1-40 | Et | — | H | K | OMe | Me | N | |
| 1-41 | Et | — | H | H | OMe | Cl | CH | |
| 1-42 | Et | — | H | Na | OMe | Cl | CH | |
| 1-43 | Et | — | H | K | OMe | Cl | CH | |
| 1-44 | Et | — | H | NH₄ | OMe | Cl | CH | |
| 1-45 | Et | — | H | H | Me | Me | CH | |
| 1-46 | Et | — | H | Na | Me | Me | CH | |
| 1-47 | Et | — | H | H | OCH₂CF₃ | NMe₂ | CH | |
| 1-48 | Et | — | H | Na | OCH₂CF₃ | NMe₂ | N | |
| 1-49 | Et | — | H | H | OMe | SMe | N | |
| 1-50 | Et | — | H | H | SMe | SMe | N | |
| 1-51 | ⁿPr | — | H | H | OMe | OMe | CH | |
| 1-52 | ⁿPr | — | H | H | OMe | OMe | N | |
| 1-53 | ⁿPr | — | H | Na | OMe | OMe | CH | |
| 1-54 | ⁿPr | — | H | K | OMe | OMe | CH | |
| 1-55 | ⁿPr | — | H | NH₄ | OMe | OMe | CH | |
| 1-56 | ⁿPr | — | H | NMe₄ | OMe | OMe | CH | |
| 1-57 | ⁿPr | — | H | Na | OMe | OMe | N | |
| 1-58 | ⁿPr | — | H | K | OMe | OMe | N | |
| 1-59 | ⁿPr | — | H | NH₄ | OMe | OMe | N | |
| 1-60 | ⁿPr | — | H | H | OMe | Me | CH | |
| 1-61 | ⁿPr | — | H | Na | OMe | Me | CH | |
| 1-62 | ⁿPr | — | H | K | OMe | Me | CH | |
| 1-63 | ⁿPr | — | H | H | OMe | Me | N | |
| 1-64 | ⁿPr | — | H | Na | OMe | Me | N | |
| 1-65 | ⁿPr | — | H | K | OMe | Me | N | |
| 1-66 | ⁿPr | — | H | H | OMe | Cl | CH | |
| 1-67 | ⁿPr | — | H | Na | OMe | Cl | CH | |
| 1-68 | ⁿPr | — | H | K | OMe | Cl | CH | |
| 1-69 | ⁿPr | — | H | NH₄ | OMe | Cl | CH | |
| 1-70 | ⁿPr | — | H | H | Me | Me | CH | |
| 1-71 | ⁿPr | — | H | Na | Me | Me | CH | |
| 1-72 | ⁿPr | — | H | H | OCH₂CF₃ | NMe₂ | N | |
| 1-73 | ⁿPr | — | H | Na | OCH₂CF₃ | NMe₂ | N | |
| 1-74 | ⁿPr | — | H | H | OMe | SMe | N | |
| 1-75 | ⁿPr | — | H | H | SMe | SMe | N | |
| 1-76 | ⁱPr | — | H | H | OMe | OMe | CH | |
| 1-77 | ⁱPr | — | H | H | OMe | OMe | N | |
| 1-78 | ⁱPr | — | H | Na | OMe | OMe | CH | |
| 1-79 | ⁱPr | — | H | K | OMe | OMe | CH | |
| 1-80 | ⁱPr | — | H | NH₄ | OMe | OMe | CH | |
| 1-81 | ⁱPr | — | H | NMe₄ | OMe | OMe | CH | |
| 1-82 | ⁱPr | — | H | Na | OMe | OMe | N | |
| 1-83 | ⁱPr | — | H | K | OMe | OMe | N | |
| 1-84 | ⁱPr | — | H | NH₄ | OMe | OMe | N | |
| 1-85 | ⁱPr | — | H | H | OMe | Me | CH | |
| 1-86 | ⁱPr | — | H | Na | OMe | Me | CH | |
| 1-87 | ⁱPr | — | H | K | OMe | Me | CH | |
| 1-88 | ⁱPr | — | H | H | OMe | Me | N | |
| 1-89 | ⁱPr | — | H | Na | OMe | Me | N | |
| 1-90 | ⁱPr | — | H | K | OMe | Me | N | |
| 1-91 | ⁱPr | — | H | H | OMe | Cl | CH | |
| 1-92 | ⁱPr | — | H | Na | OMe | Cl | CH | |
| 1-93 | ⁱPr | — | H | K | OMe | Cl | CH | |
| 1-94 | ⁱPr | — | H | NH₄ | OMe | Cl | CH | |
| 1-95 | ⁱPr | — | H | H | Me | Me | CH | |
| 1-96 | ⁱPr | — | H | Na | Me | Me | CH | |
| 1-97 | ⁱPr | — | H | H | OCH₂CF₃ | NMe₂ | N | |
| 1-98 | ⁱPr | — | H | Na | OCH₂CF₃ | NMe₂ | N | |
| 1-99 | ⁱPr | — | H | H | OMe | SMe | N | |
| 1-100 | ⁱPr | — | H | H | SMe | SMe | N | |

TABLE 1-continued

Compounds of the formula (Ia)

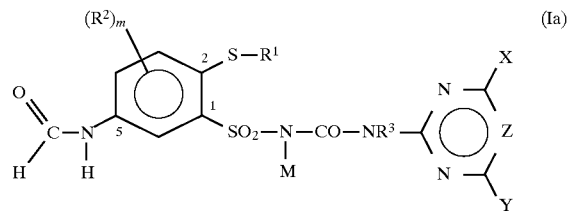

| Example number | R¹ | (R²)ₘ | R³ | M | X | Y | Z | m.p. |
|---|---|---|---|---|---|---|---|---|
| 1-101 | cPr | — | H | H | OMe | OMe | CH | |
| 1-102 | cPr | — | H | Na | OMe | OMe | CH | |
| 1-103 | cPr | — | H | H | OMe | Me | CH | |
| 1-104 | cPr | — | H | H | OMe | Cl | CH | |
| 1-105 | cPr | — | H | H | Me | Me | CH | |
| 1-106 | cPr | — | H | H | OMe | OMe | N | |
| 1-107 | cPr | — | H | H | Me | Me | N | |
| 1-108 | cPr | — | H | H | OCH$_2$CF$_3$ | NMe$_2$ | N | |
| 1-109 | CH$_2$—cPr | — | H | H | OMe | OMe | CH | |
| 1-110 | CH$_2$F | — | H | H | OMe | OMe | CH | |
| 1-111 | CF$_3$ | — | H | H | OMe | OMe | CH | |
| 1-112 | CH$_2$Cl | — | H | H | OMe | OMe | CH | |
| 1-113 | CH$_2$CH$_2$F | — | H | H | OMe | OMe | CH | |
| 1-114 | CH$_2$CF$_3$ | — | H | H | OMe | OMe | CH | |
| 1-115 | CH$_2$CH$_2$OMe | — | H | H | OMe | OMe | CH | |
| 1-116 | CH$_2$CH$_2$SMe | — | H | H | OMe | OMe | CH | |
| 1-117 | —CH=CH$_2$ | — | H | H | OMe | OMe | CH | |
| 1-118 | CH$_2$CH=CH$_2$ | — | H | H | OMe | OMe | CH | |
| 1-119 | Ph | — | H | H | OMe | OMe | CH | |
| 1-120 | thiophen-2-yl | — | H | H | OMe | OMe | CH | |
| 1-121 | thiophen-3-yl | — | H | H | OMe | OMe | CH | |
| 1-122 | pyrrol-2-yl | — | H | H | OMe | OMe | CH | |
| 1-123 | pyrrol-3-yl | — | H | H | OMe | OMe | CH | |
| 1-124 | Me | 4-F | H | H | OMe | OMe | CH | |
| 1-125 | Me | 4-Cl | H | H | OMe | OMe | CH | |
| 1-126 | Me | 4-OMe | H | H | OMe | OMe | CH | |
| 1-127 | Me | 4-Me | H | H | OMe | OMe | CH | |
| 1-127 | Me | 4-Me | H | H | OMe | OMe | CH | |
| 1-128 | Me | — | Me | Na | OMe | OMe | CH | |
| 1-129 | CH$_2$CO$_2$Me | — | H | H | OMe | OMe | CH | |
| 1-130 | CH$_2$CH$_2$NH$_2$ | — | H | H | OMe | OMe | CH | |
| 1-131 | CH$_2$SMe | — | H | H | OMe | OMe | CH | |
| 1-132 | CMe$_3$ | — | H | H | OMe | OMe | CH | |
| 1-133 | Cyclohexyl | — | H | H | OMe | OMe | CH | |
| 1-134 | Cyclobutyl | — | H | H | OMe | OMe | CH | |
| 1-134 | Cyclopentyl | — | H | H | OMe | OMe | CH | |
| 1-135 | Me | — | OMe | H | OMe | OMe | CH | |
| 1-136 | Et | — | Me | H | OMe | OMe | CH | |
| 1-137 | Et | — | Me | Na | OMe | OMe | CH | |
| 1-138 | Me | — | Me | H | OMe | Me | N | |
| 1-139 | Me | — | Me | Na | OMe | Me | N | |
| 1-140 | CH$_2$COCH$_3$ | — | H | H | OMe | Me | CH | |

TABLE 2

Compounds of the formula (Ib)

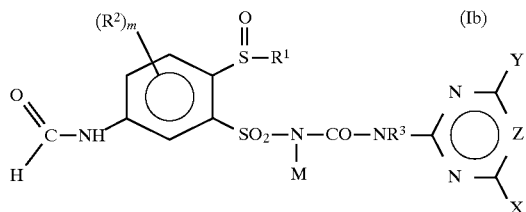

| Example number | $R^1$ | $(R^2)_m$ | $R^3$ | M | X | Y | Z | m.p. |
|---|---|---|---|---|---|---|---|---|
| 2-1 | Me | — | H | H | OMe | OMe | CH | |
| 2-2 | Me | — | H | H | OMe | OMe | N | |
| 2-3 | Me | — | H | Na | OMe | OMe | CH | |
| 2-4 | Me | — | H | K | OMe | OMe | CH | |
| 2-5 | Me | — | H | $NH_4$ | OMe | OMe | CH | |
| 2-6 | Me | — | H | $NMe_4$ | OMe | OMe | CH | |
| 2-7 | Me | — | H | Na | OMe | OMe | N | |
| 2-8 | Me | — | H | K | OMe | OMe | N | |
| 2-9 | Me | — | H | $NH_4$ | OMe | OMe | N | |
| 2-10 | Me | — | H | H | OMe | Me | CH | |
| 2-11 | Me | — | H | Na | OMe | Me | CH | |
| 2-12 | Me | — | H | K | OMe | Me | CH | |
| 2-13 | Me | — | H | H | OMe | Me | N | |
| 2-14 | Me | — | H | Na | OMe | Me | N | |
| 2-15 | Me | — | H | K | OMe | Me | N | |
| 2-16 | Me | — | H | H | OMe | Cl | CH | |
| 2-17 | Me | — | H | Na | OMe | Cl | CH | |
| 2-18 | Me | — | H | K | OMe | Cl | CH | |
| 2-19 | Me | — | H | $NH_4$ | OMe | Cl | CH | |
| 2-20 | Me | — | H | H | Me | Me | CH | |
| 2-21 | Me | — | H | Na | Me | Me | CH | |
| 2-22 | Me | — | H | H | $OCH_2CF_3$ | $NMe_2$ | N | |
| 2-23 | Me | — | H | Na | $OCH_2CF_3$ | $NMe_2$ | N | |
| 2-24 | Me | — | H | H | OMe | SMe | N | |
| 2-25 | Me | — | H | H | SMe | SMe | N | |
| 2-26 | Et | — | H | H | OMe | OMe | CH | 85–9 (d) |
| 2-27 | Et | — | H | H | OMe | OMe | N | |
| 2-28 | Et | — | H | Na | OMe | OMe | CH | |
| 2-29 | Et | — | H | K | OMe | OMe | CH | |
| 2-30 | Et | — | H | $NH_4$ | OMe | OMe | CH | |
| 2-31 | Et | — | H | $NMe_4$ | OMe | OMe | CH | |
| 2-32 | Et | — | H | Na | OMe | OMe | N | |
| 2-33 | Et | — | H | K | OMe | OMe | N | |
| 2-34 | Et | — | H | $NH_4$ | OMe | OMe | N | |
| 2-35 | Et | — | H | H | OMe | Me | CH | |
| 2-36 | Et | — | H | Na | OMe | Me | CH | |
| 2-37 | Et | — | H | K | OMe | Me | CH | |
| 2-38 | Et | — | H | H | OMe | Me | N | |
| 2-39 | Et | — | H | Na | OMe | Me | N | |
| 2-40 | Et | — | H | K | OMe | Me | N | |
| 2-41 | Et | — | H | H | OMe | Cl | CH | |
| 2-42 | Et | — | H | Na | OMe | Cl | CH | |
| 2-43 | Et | — | H | K | OMe | Cl | CH | |
| 2-44 | Et | — | H | $NH_4$ | OMe | Cl | CH | |
| 2-45 | Et | — | H | H | Me | Me | CH | |
| 2-46 | Et | — | H | Na | Me | Me | CH | |
| 2-47 | Et | — | H | H | $OCH_2CF_3$ | $NMe_2$ | N | |
| 2-48 | Et | — | H | Na | $OCH_2CF_3$ | $NMe_2$ | N | |
| 2-49 | Et | — | H | H | OMe | SMe | N | |
| 2-50 | Et | — | H | H | SMe | SMe | N | |
| 2-51 | $^nPr$ | — | H | H | OMe | OMe | CH | |
| 2-52 | $^nPr$ | — | H | H | OMe | OMe | N | |
| 2-53 | $^nPr$ | — | H | Na | OMe | OMe | CH | |
| 2-54 | $^nPr$ | — | H | K | OMe | OMe | CH | |
| 2-55 | $^nPr$ | — | H | $NH_4$ | OMe | OMe | CH | |
| 2-56 | $^nPr$ | — | H | $NMe_4$ | OMe | OMe | CH | |
| 2-57 | $^nPr$ | — | H | Na | OMe | OMe | N | |
| 2-58 | $^nPr$ | — | H | K | OMe | OMe | N | |
| 2-59 | $^nPr$ | — | H | $NH_4$ | OMe | OMe | N | |
| 2-60 | $^nPr$ | — | H | H | OMe | Me | CH | |
| 2-61 | $^nPr$ | — | H | Na | OMe | Me | CH | |
| 2-62 | $^nPr$ | — | H | K | OMe | Me | CH | |

TABLE 2-continued

Compounds of the formula (Ib)

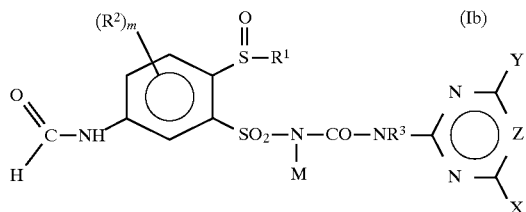

| Example number | $R^1$ | $(R^2)_m$ | $R^3$ | M | X | Y | Z | m.p. |
|---|---|---|---|---|---|---|---|---|
| 2-63 | $^nPr$ | — | H | H | OMe | Me | N | |
| 2-64 | $^nPr$ | — | H | Na | OMe | Me | N | |
| 2-65 | $^nPr$ | — | H | K | OMe | Me | N | |
| 2-66 | $^nPr$ | — | H | H | OMe | Cl | CH | |
| 2-67 | $^nPr$ | — | H | Na | OMe | Cl | CH | |
| 2-68 | $^nPr$ | — | H | K | OMe | Cl | CH | |
| 2-69 | $^nPr$ | — | H | $NH_4$ | OMe | Cl | CH | |
| 2-70 | $^nPr$ | — | H | H | Me | Me | CH | |
| 2-71 | $^nPr$ | — | H | Na | Me | Me | CH | |
| 2-72 | $^nPr$ | — | H | H | $OCH_2CF_3$ | $NMe_2$ | N | |
| 2-73 | $^nPr$ | — | H | Na | $OCH_2CF_3$ | $NMe_2$ | N | |
| 2-74 | $^nPr$ | — | H | H | OMe | SMe | N | |
| 2-75 | $^nPr$ | — | H | H | SMe | SMe | N | |
| 2-76 | $^iPr$ | — | H | H | OMe | OMe | CH | |
| 2-77 | $^iPr$ | — | H | H | OMe | OMe | N | |
| 2-78 | $^iPr$ | — | H | Na | OMe | OMe | CH | |
| 2-79 | $^iPr$ | — | H | K | OMe | OMe | CH | |
| 2-80 | $^iPr$ | — | H | $NH_4$ | OMe | OMe | CH | |
| 2-81 | $^iPr$ | — | H | $NMe_4$ | OMe | OMe | CH | |
| 2-82 | $^iPr$ | — | H | Na | OMe | OMe | N | |
| 2-83 | $^iPr$ | — | H | K | OMe | OMe | N | |
| 2-84 | $^iPr$ | — | H | $NH_4$ | OMe | OMe | N | |
| 2-85 | $^iPr$ | — | H | H | OMe | Me | CH | |
| 2-86 | $^iPr$ | — | H | Na | OMe | Me | CH | |
| 2-87 | $^iPr$ | — | H | K | OMe | Me | CH | |
| 2-88 | $^iPr$ | — | H | H | OMe | Me | N | |
| 2-89 | $^iPr$ | — | H | Na | OMe | Me | N | |
| 2-90 | $^iPr$ | — | H | K | OMe | Me | N | |
| 2-91 | $^iPr$ | — | H | H | OMe | Cl | CH | |
| 2-92 | $^iPr$ | — | H | Na | OMe | Cl | CH | |
| 2-93 | $^iPr$ | — | H | K | OMe | Cl | CH | |
| 2-94 | $^iPr$ | — | H | $NH_4$ | OMe | Cl | CH | |
| 2-95 | $^iPr$ | — | H | H | Me | Me | CH | |
| 2-96 | $^iPr$ | — | H | Na | Me | Me | CH | |
| 2-97 | $^iPr$ | — | H | H | $OCH_2CF_3$ | $NMe_2$ | N | |
| 2-98 | $^iPr$ | — | H | Na | $OCH_2CF_3$ | $NMe_2$ | N | |
| 2-99 | $^iPr$ | — | H | H | OMe | SMe | N | |
| 2-100 | $^iPr$ | — | H | H | SMe | SMe | N | |
| 2-101 | $^cPr$ | — | H | H | OMe | OMe | CH | |
| 2-102 | $^cPr$ | — | H | Na | OMe | OMe | CH | |
| 2-103 | $^cPr$ | — | H | H | OMe | Me | CH | |
| 2-104 | $^cPr$ | — | H | H | OMe | Cl | CH | |
| 2-105 | $^cPr$ | — | H | H | Me | Me | CH | |
| 2-106 | $^cPr$ | — | H | H | OMe | OMe | N | |
| 2-107 | $^cPr$ | — | H | H | OMe | Me | N | |
| 2-108 | $^cPr$ | — | H | H | $OCH_2CF_3$ | $NMe_2$ | N | |
| 2-109 | $CH_2$—$^cPr$ | — | H | H | OMe | OMe | CH | |
| 2-110 | $CH_2F$ | — | H | H | OMe | OMe | CH | |
| 2-111 | $CF_3$ | — | H | H | OMe | OMe | CH | |
| 2-112 | $CH_2Cl$ | — | H | H | OMe | OMe | CH | |
| 2-113 | $CH_2CH_2F$ | — | H | H | OMe | OMe | CH | |
| 2-114 | $CH_2CF_3$ | — | H | H | OMe | OMe | CH | |
| 2-115 | $CH_2CH_2OMe$ | — | H | H | OMe | OMe | CH | |
| 2-116 | $CH_2CH_2SMe$ | — | H | H | OMe | OMe | CH | |
| 2-117 | $CH=CH_2$ | — | H | H | OMe | OMe | CH | |
| 2-118 | $CH_2CH=CH_2$ | — | H | H | OMe | OMe | CH | |
| 2-119 | Ph | — | H | H | OMe | OMe | CH | |
| 2-120 | thiophen-2-yl | — | H | H | OMe | OMe | CH | |
| 2-121 | thiophen-3-yl | — | H | H | OMe | OMe | CH | |
| 2-122 | pyrrol-2-yl | — | H | H | OMe | OMe | CH | |
| 2-123 | pyrrol-3-yl | — | H | H | OMe | OMe | CH | |
| 2-124 | $NMe_2$ | — | H | H | OMe | OMe | CH | |

TABLE 2-continued

Compounds of the formula (Ib)

| Example number | R¹ | (R²)ₘ | R³ | M | X | Y | Z | m.p. |
|---|---|---|---|---|---|---|---|---|
| 2-125 | NMe₂ | — | H | H | OMe | OMe | N | |
| 2-126 | NMe₂ | — | H | Na | OMe | OMe | CH | |
| 2-127 | NMe₂ | — | H | K | OMe | OMe | CH | |
| 2-128 | NMe₂ | — | H | NH₄ | OMe | OMe | CH | |
| 2-129 | NMe₂ | — | H | NMe₄ | OMe | OMe | CH | |
| 2-130 | NMe₂ | — | H | Na | OMe | OMe | N | |
| 2-131 | NMe₂ | — | H | K | OMe | OMe | N | |
| 2-132 | NMe₂ | — | H | NH₄ | OMe | OMe | N | |
| 2-133 | NMe₂ | — | H | H | OMe | Me | CH | |
| 2-134 | NMe₂ | — | H | Na | OMe | Me | CH | |
| 2-135 | NMe₂ | — | H | K | OMe | Me | CH | |
| 2-136 | NMe₂ | — | H | H | OMe | Me | N | |
| 2-137 | NMe₂ | — | H | Na | OMe | Me | N | |
| 2-138 | NMe₂ | — | H | K | OMe | Me | N | |
| 2-139 | NMe₂ | — | H | H | OMe | Cl | CH | |
| 2-140 | NMe₂ | — | H | Na | OMe | Cl | CH | |
| 2-141 | NMe₂ | — | H | K | OMe | Cl | CH | |
| 2-142 | NMe₂ | — | H | NH₄ | OMe | Cl | CH | |
| 2-143 | NMe₂ | — | H | H | Me | Me | CH | |
| 2-144 | NMe₂ | — | H | Na | Me | Me | CH | |
| 2-145 | NMe₂ | — | H | H | OCH₂CF₃ | NMe₂ | N | |
| 2-146 | NMe₂ | — | H | Na | OCH₂CF₃ | NMe₂ | N | |
| 2-147 | NMe₂ | — | H | H | OMe | SMe | N | |
| 2-148 | NMe₂ | — | H | H | SMe | SMe | N | |
| 2-149 | NHMe | — | H | H | OMe | OMe | CH | |
| 2-150 | NHMe | — | H | Na | OMe | OMe | CH | |
| 2-151 | NHMe | — | H | H | OMe | OMe | N | |
| 2-152 | NHMe | — | H | H | OMe | Me | N | |
| 2-153 | NHMe | — | H | H | OMe | Cl | CH | |
| 2-154 | NHMe | — | H | H | OCH₂CF₃ | NMe₂ | N | |
| 2-155 | NEt₂ | — | H | H | OMe | OMe | CH | |
| 2-156 | pyrrolidin-1-yl | — | H | H | OMe | OMe | CH | |
| 2-157 | morpholin-4-yl | — | H | H | OMe | OMe | CH | |
| 2-158 | OMe | — | H | H | OMe | OMe | CH | |
| 2-159 | OEt | — | H | H | OMe | OMe | CH | |
| 2-160 | OCH₂CF₃ | — | H | H | OMe | OMe | CH | |
| 2-161 | OCH₂CCl₃ | — | H | H | OMe | OMe | CH | |
| 2-162 | OⁱPr | — | H | H | OMe | OMe | CH | |
| 2-163 | —O—ᶜPr | — | H | H | OMe | OMe | CH | |
| 2-164 | Me | 4-F | H | H | OMe | OMe | CH | |
| 2-165 | Me | 4-Cl | H | H | OMe | OMe | CH | |
| 2-166 | Me | 3-F | H | H | OMe | OMe | CH | |
| 2-167 | Me | 3-Me | H | H | OMe | OMe | CH | |
| 2-168 | Me | 3-OMe | H | H | OMe | OMe | CH | |
| 2-169 | Me | 4-NMe₂ | H | H | OMe | OMe | CH | |
| 2-170 | Me | 4-NO₂ | H | H | OMe | OMe | CH | |
| 2-171 | Me | — | Me | H | OMe | OMe | CH | |
| 2-172 | Me | — | Me | Na | OMe | OMe | CH | |
| 2-173 | Me | — | Me | H | OMe | Me | N | |
| 2-174 | Me | — | Me | Na | OMe | Me | N | |

TABLE 3

Compounds of the formula (Ic)

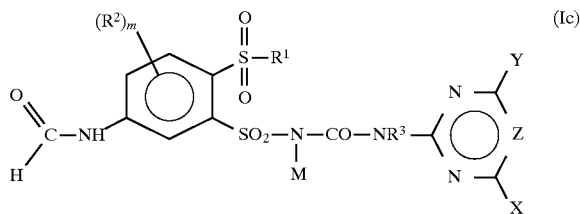

| Example number | R¹ | (R²)ₘ | R³ | M | X | Y | Z | m.p. |
|---|---|---|---|---|---|---|---|---|
| 3-1 | Me | — | H | H | OMe | OMe | CH | |
| 3-2 | Me | — | H | H | OMe | OMe | N | |
| 3-3 | Me | — | H | Na | OMe | OMe | CH | |
| 3-4 | Me | — | H | K | OMe | OMe | CH | |
| 3-5 | Me | — | H | NH₄ | OMe | OMe | CH | |
| 3-6 | Me | — | H | NMe₄ | OMe | OMe | CH | |
| 3-7 | Me | — | H | Na | OMe | OMe | N | |
| 3-8 | Me | — | H | K | OMe | OMe | N | |
| 3-9 | Me | — | H | NH₄ | OMe | OMe | N | |
| 3-10 | Me | — | H | H | OMe | Me | CH | |
| 3-11 | Me | — | H | Na | OMe | Me | CH | |
| 3-12 | Me | — | H | K | OMe | Me | CH | |
| 3-13 | Me | — | H | H | OMe | Me | N | 190–2 (d) |
| 3-14 | Me | — | H | Na | OMe | Me | N | |
| 3-15 | Me | — | H | K | OMe | Me | N | |
| 3-16 | Me | — | H | H | OMe | Cl | CH | 137–8 (d) |
| 3-17 | Me | — | H | Na | OMe | Cl | CH | |
| 3-18 | Me | — | H | K | OMe | Cl | CH | |
| 3-19 | Me | — | H | NH₄ | OMe | Cl | CH | |
| 3-20 | Me | — | H | H | Me | Me | CH | |
| 3-21 | Me | — | H | Na | Me | Me | CH | |
| 3-22 | Me | — | H | H | OCH₂CF₃ | NMe₂ | N | |
| 3-23 | Me | — | H | Na | OCH₂CF₃ | NMe₂ | N | |
| 3-24 | Me | — | H | H | OMe | SMe | N | |
| 3-25 | Me | — | H | H | SMe | SMe | N | |
| 3-26 | Et | — | H | H | OMe | OMe | CH | 152 (d) |
| 3-27 | Et | — | H | H | OMe | OMe | N | |
| 3-28 | Et | — | H | Na | OMe | OMe | CH | 197–202 (d) |
| 3-29 | Et | — | H | K | OMe | OMe | CH | |
| 3-30 | Et | — | H | NH₄ | OMe | OMe | CH | |
| 3-31 | Et | — | H | NMe₄ | OMe | OMe | CH | |
| 3-32 | Et | — | H | Na | OMe | OMe | N | |
| 3-33 | Et | — | H | K | OMe | OMe | N | |
| 3-34 | Et | — | H | NH₄ | OMe | OMe | N | |
| 3-35 | Et | — | H | H | OMe | Me | CH | |
| 3-36 | Et | — | H | Na | OMe | Me | CH | |
| 3-37 | Et | — | H | K | OMe | Me | CH | |
| 3-38 | Et | — | H | H | OMe | Me | N | |
| 3-39 | Et | — | H | Na | OMe | Me | N | |
| 3-40 | Et | — | H | K | OMe | Me | N | |
| 3-41 | Et | — | H | H | OMe | Cl | CH | |
| 3-42 | Et | — | H | Na | OMe | Cl | CH | |
| 3-43 | Et | — | H | K | OMe | Cl | CH | |
| 3-44 | Et | — | H | NH₄ | OMe | Cl | CH | |
| 3-45 | Et | — | H | H | Me | Me | CH | |
| 3-46 | Et | — | H | Na | Me | Me | CH | |
| 3-47 | Et | — | H | H | OCH₂CF₃ | NMe₂ | N | |
| 3-48 | Et | — | H | Na | OCH₂CF₃ | NMe₂ | N | |
| 3-49 | Et | — | H | H | OMe | SMe | N | |
| 3-50 | Et | — | H | H | SMe | SMe | N | |
| 3-51 | ⁿPr | — | H | H | OMe | OMe | CH | 200–202 (d) |
| 3-52 | ⁿPr | — | H | H | OMe | OMe | N | |
| 3-53 | ⁿPr | — | H | Na | OMe | OMe | CH | |
| 3-54 | ⁿPr | — | H | K | OMe | OMe | CH | |
| 3-55 | ⁿPr | — | H | NH₄ | OMe | OMe | CH | |
| 3-56 | ⁿPr | — | H | NMe₄ | OMe | OMe | CH | |
| 3-57 | ⁿPr | — | H | Na | OMe | OMe | N | |
| 3-58 | ⁿPr | — | H | K | OMe | OMe | N | |
| 3-59 | ⁿPr | — | H | NH₄ | OMe | OMe | N | |
| 3-60 | ⁿPr | — | H | H | OMe | Me | CH | |

TABLE 3-continued

Compounds of the formula (Ic)

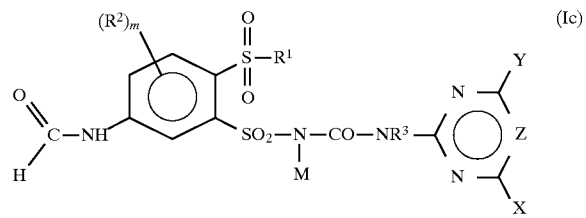

| Example number | $R^1$ | $(R^2)_m$ | $R^3$ | M | X | Y | Z | m.p. |
|---|---|---|---|---|---|---|---|---|
| 3-61 | $^nPr$ | — | H | Na | OMe | Me | CH | |
| 3-62 | $^nPr$ | — | H | K | OMe | Me | CH | |
| 3-63 | $^nPr$ | — | H | H | OMe | Me | N | |
| 3-64 | $^nPr$ | — | H | Na | OMe | Me | N | |
| 3-65 | $^nPr$ | — | H | K | OMe | Me | N | |
| 3-66 | $^nPr$ | — | H | H | OMe | Cl | CH | |
| 3-67 | $^nPr$ | — | H | Na | OMe | Cl | CH | |
| 3-68 | $^nPr$ | — | H | K | OMe | Cl | CH | |
| 3-69 | $^nPr$ | — | H | $NH_4$ | OMe | Cl | CH | |
| 3-70 | $^nPr$ | — | H | H | Me | Me | CH | |
| 3-71 | $^nPr$ | — | H | Na | Me | Me | CH | |
| 3-72 | $^nPr$ | — | H | H | $OCH_2CF_3$ | $NMe_2$ | N | |
| 3-73 | $^nPr$ | — | H | Na | $OCH_2CF_3$ | $NMe_2$ | N | |
| 3-74 | $^nPr$ | — | H | H | OMe | SMe | N | |
| 3-75 | $^nPr$ | — | H | H | SMe | SMe | N | |
| 3-76 | $^iPr$ | — | H | H | OMe | OMe | CH | 159–162 (d) |
| 3-77 | $^iPr$ | — | H | H | OMe | OMe | N | |
| 3-78 | $^iPr$ | — | H | Na | OMe | OMe | CH | |
| 3-79 | $^iPr$ | — | H | K | OMe | OMe | CH | |
| 3-80 | $^iPr$ | — | H | $NH_4$ | OMe | OMe | CH | |
| 3-81 | $^iPr$ | — | H | $NMe_4$ | OMe | OMe | CH | |
| 3-82 | $^iPr$ | — | H | Na | OMe | OMe | N | |
| 3-83 | $^iPr$ | — | H | K | OMe | OMe | N | |
| 3-84 | $^iPr$ | — | H | $NH_4$ | OMe | OMe | N | |
| 3-85 | $^iPr$ | — | H | H | OMe | Me | CH | |
| 3-86 | $^iPr$ | — | H | Na | OMe | Me | CH | |
| 3-87 | $^iPr$ | — | H | K | OMe | Me | CH | |
| 3-88 | $^iPr$ | — | H | H | OMe | Me | N | |
| 3-89 | $^iPr$ | — | H | Na | OMe | Me | N | |
| 3-90 | $^iPr$ | — | H | K | OMe | Me | N | |
| 3-91 | $^iPr$ | — | H | H | OMe | Cl | CH | |
| 3-92 | $^iPr$ | — | H | Na | OMe | Cl | CH | |
| 3-93 | $^iPr$ | — | H | K | OMe | Cl | CH | |
| 3-94 | $^iPr$ | — | H | $NH_4$ | OMe | Cl | CH | |
| 3-95 | $^iPr$ | — | H | H | Me | Me | CH | |
| 3-96 | $^iPr$ | — | H | Na | Me | Me | CH | |
| 3-97 | $^iPr$ | — | H | H | $OCH_2CF_3$ | $NMe_2$ | N | |
| 3-98 | $^iPr$ | — | H | Na | $OCH_2CF_3$ | $NMe_2$ | N | |
| 3-99 | $^iPr$ | — | H | H | OMe | SMe | N | |
| 3-100 | $^iPr$ | — | H | H | OMe | SMe | N | |
| 3-101 | $NMe_2$ | — | H | H | OMe | OMe | CH | 158–160 (d) |
| 3-102 | $NMe_2$ | — | H | H | OMe | OMe | N | |
| 3-103 | $NMe_2$ | — | H | Na | OMe | OMe | CH | 165 (d) |
| 3-104 | $NMe_2$ | — | H | K | OMe | OMe | CH | |
| 3-105 | $NMe_2$ | — | H | $NH_4$ | OMe | OMe | CH | |
| 3-106 | $NMe_2$ | — | H | $NMe_4$ | OMe | OMe | CH | |
| 3-107 | $NMe_2$ | — | H | Na | OMe | OMe | N | |
| 3-108 | $NMe_2$ | — | H | K | OMe | OMe | N | |
| 3-109 | $NMe_2$ | — | H | $NH_4$ | OMe | OMe | N | |
| 3-110 | $NMe_2$ | — | H | H | OMe | Me | CH | |
| 3-111 | $NMe_2$ | — | H | Na | OMe | Me | CH | |
| 3-112 | $NMe_2$ | — | H | K | OMe | Me | CH | |
| 3-113 | $NMe_2$ | — | H | H | OMe | Me | N | |
| 3-114 | $NMe_2$ | — | H | Na | OMe | Me | N | |
| 3-115 | $NMe_2$ | — | H | K | OMe | Me | N | |
| 3-116 | $NMe_2$ | — | H | H | OMe | Cl | CH | |
| 3-117 | $NMe_2$ | — | H | Na | OMe | Cl | CH | |
| 3-118 | $NMe_2$ | — | H | K | OMe | Cl | CH | |
| 3-119 | $NMe_2$ | — | H | $NH_4$ | OMe | Cl | CH | |
| 3-120 | $NMe_2$ | — | H | H | Me | Me | CH | |

TABLE 3-continued

Compounds of the formula (Ic)

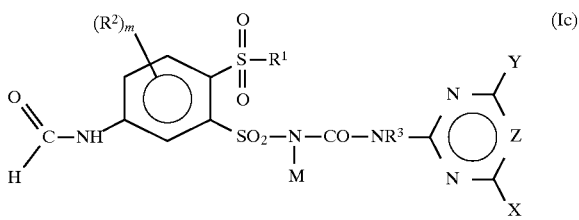

| Example number | $R^1$ | $(R^2)_m$ | $R^3$ | M | X | Y | Z | m.p. |
|---|---|---|---|---|---|---|---|---|
| 3-121 | NMe$_2$ | — | H | Na | Me | Me | CH | |
| 3-122 | NMe$_2$ | — | H | H | OCH$_2$CF$_3$ | NMe$_2$ | N | |
| 3-123 | NMe$_2$ | — | H | Na | OCH$_2$CF$_3$ | NMe$_2$ | N | |
| 3-124 | NMe$_2$ | — | H | H | OMe | SMe | N | |
| 3-125 | NMe$_2$ | — | H | H | SMe | SMe | N | |
| 3-126 | $^c$Pr | — | H | H | OMe | OMe | CH | |
| 3-127 | $^c$Pr | — | H | Na | OMe | OMe | CH | |
| 3-128 | $^c$Pr | — | H | H | OMe | Me | CH | |
| 3-129 | $^c$Pr | — | H | H | OMe | Cl | CH | |
| 3-130 | $^c$Pr | — | H | H | Me | Me | CH | |
| 3-131 | $^c$Pr | — | H | H | OMe | OMe | N | |
| 3-132 | $^c$Pr | — | H | H | OMe | Me | N | |
| 3-133 | $^c$Pr | — | H | H | OCH$_2$CF$_3$ | NMe$_2$ | N | |
| 3-134 | CH$_2$—$^c$Pr | — | H | H | OMe | OMe | CH | |
| 3-135 | CH$_2$F | — | H | H | OMe | OMe | CH | |
| 3-136 | CF$_3$ | — | H | H | OMe | OMe | CH | |
| 3-137 | CH$_2$Cl | — | H | H | OMe | OMe | CH | |
| 3-138 | CH$_2$CH$_2$F | — | H | H | OMe | OMe | CH | |
| 3-139 | CH$_2$CF$_3$ | — | H | H | OMe | OMe | CH | |
| 3-140 | CH$_2$CH$_2$OMe | — | H | H | OMe | OMe | CH | |
| 3-141 | CH$_2$CH$_2$SMe | — | H | H | OMe | OMe | CH | |
| 3-142 | CH=CH$_2$ | — | H | H | OMe | OMe | CH | |
| 3-143 | CH$_2$CH=CH$_2$ | — | H | H | OMe | OMe | CH | |
| 3-144 | Ph | — | H | H | OMe | OMe | CH | |
| 3-145 | thiophen-2-yl | — | H | H | OMe | OMe | CH | |
| 3-146 | thiophen-3-yl | — | H | H | OMe | OMe | CH | |
| 3-147 | pyrrol-2-yl | — | H | H | OMe | OMe | CH | |
| 3-148 | pyrrol-3-yl | — | H | H | OMe | OMe | CH | |
| 3-149 | NHMe | — | H | H | OMe | OMe | CH | |
| 3-150 | NHMe | — | H | Na | OMe | OMe | CH | |
| 3-151 | NHMe | — | H | H | OMe | OMe | N | |
| 3-152 | NHMe | — | H | H | OMe | Me | N | |
| 3-153 | NHMe | — | H | H | OMe | Cl | CH | |
| 3-154 | NHMe | — | H | H | OCH$_2$CF$_3$ | NMe$_2$ | N | |
| 3-155 | NEt$_2$ | — | H | H | OMe | OMe | CH | |
| 3-156 | pyrrolidin-1-yl | — | H | H | OMe | OMe | CH | |
| 3-157 | N-morpholin-4-yl | — | H | H | OMe | OMe | CH | |
| 3-158 | OMe | — | H | H | OMe | OMe | CH | |
| 3-159 | OEt | — | H | H | OMe | OMe | CH | |
| 3-160 | OCH$_2$CF$_3$ | — | H | H | OMe | OMe | CH | |
| 3-161 | OCH$_2$CCl$_3$ | — | H | H | OMe | OMe | CH | |
| 3-162 | O$^i$Pr | — | H | H | OMe | OMe | CH | |
| 3-163 | —O$^c$Pr | — | H | H | OMe | OMe | CH | |
| 3-164 | Me | — | Me | H | OMe | OMe | CH | |
| 3-165 | Me | — | Me | H | OMe | Me | N | |
| 3-166 | Et | — | Me | H | OMe | Me | N | |
| 3-167 | Et | — | Me | H | OMe | OMe | CH | |
| 3-168 | OH | — | H | H | OMe | OMe | CH | |
| 3-169 | OH | — | H | H | OMe | Me | N | |
| 3-170 | C≡C | — | H | H | OMe | OMe | CH | |
| 3-171 | CH$_2$C≡CH | — | H | H | OMe | OMe | CH | |
| 3-172 | CH$_2$CH=CF$_2$ | — | H | H | OMe | OMe | CH | |
| 3-173 | OH | — | H | H | OMe | OMe | CH | |
| 3-174 | NHOH | — | H | H | OMe | OMe | CH | |
| 3-175 | NHOMe | — | H | H | OMe | OMe | CH | |
| 3-176 | NHOEt | — | H | H | OMe | OMe | CH | |
| 3-177 | NHNH$_2$ | — | H | H | OMe | OMe | CH | |
| 3-178 | NMeNMe$_2$ | — | H | H | OMe | OMe | CH | |
| 3-179 | NHNMe$_2$ | — | H | H | OMe | OMe | CH | |
| 3-180 | N(OMe)Me | — | H | H | OMe | OMe | CH | |

TABLE 3-continued

Compounds of the formula (Ic)

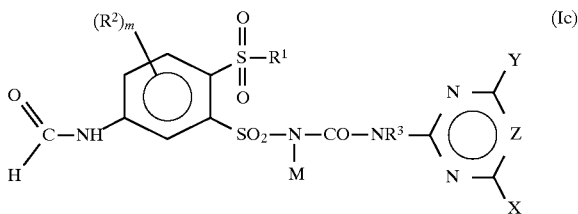

| Example number | R¹ | (R²)ₘ | R³ | M | X | Y | Z | m.p. |
|---|---|---|---|---|---|---|---|---|
| 3-181 | CH₂CH₂SO₂Me | — | H | H | OMe | OMe | CH | |
| 3-182 | CH₂COCH₃ | — | H | H | OMe | OMe | CH | |
| 3-183 | CH₂COOMe | — | H | H | OMe | OMe | CH | |
| 3-184 | CH₂CO—NMe₂ | — | H | H | OMe | OMe | CH | |
| 3-184 | CH₂—CN | — | H | H | OMe | OMe | CH | |

TABLE 4

Compounds of the formula (Id)

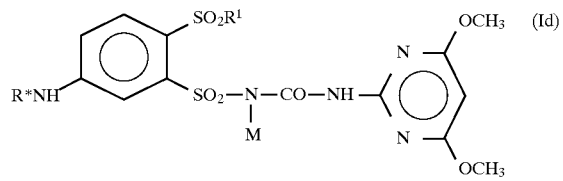

| Example number | R* | R¹ | M | m.p. |
|---|---|---|---|---|
| 4-1 | CHO | NHCH₂CH₂N(CH₃)₂ | H | |
| 4-2 | CHO | NHCONH₂ | H | |
| 4-3 | CHO | NHCONHCH₃ | H | |
| 4-4 | CHO | NHCON(CH₃)₂ | H | |
| 4-5 | CHO | NHCOCH₃ | H | |
| 4-6 | CHO | NHCO₂CH₃ | H | |
| 4-7 | CHO | NHCO₂NHCH₃ | H | |
| 4-8 | CHO | CH₂NHCONH₂ | H | |
| 4-9 | CHO | (CH₂)₅CH₃ | H | |
| 4-10 | CHO | CH₂COCH₃ | H | |
| 4-11 | CHO | CH₂CONH₂ | H | |
| 4-12 | CHO | CH₂CO₂CH₃ | H | |
| 4-13 | CHO | CH₂NO₂ | H | |
| 4-14 | CH=NH | CH₃ | H | |
| 4-15 | CH=NH | C₂H₅ | H | |
| 4-16 | CH=NH | C₂H₅ | Na | |
| 4-17 | CH=NH | CH(CH₃)₂ | H | |
| 4-18 | CH=NH | CH₂CH₂CH₃ | H | |
| 4-19 | CH=NCH₃ | CH₃ | H | |
| 4-20 | CH=NCH₃ | C₂H₅ | H | |
| 4-21 | CH(OCH₃)₂ | CH₃ | H | |
| 4-22 | CH(OEt)₂ | CH₃ | H | |
| 4-23 | CH(OEt)₂ | C₂H₅ | H | |
| 4-24 | CH(OEt)₂ | CH₃ | H | |
| 4-25 | CH(OEt)₂ | CH₃ | Na | |
| 4-26 | CH(OEt)₂ | C₂H₅ | H | |
| 4-27 | CH(OEt)₂ | C₂H₅ | Na | |
| 4-28 | CH=N—OH | CH₃ | H | |
| 4-29 | CH=N—OH | CH₃ | Na | |
| 4-30 | CH=N—OCH₃ | CH₃ | H | |
| 4-31 | CH=N—NH₂ | CH₃ | H | |
| 4-32 | CH=N—NHPh | CH₃ | H | |
| 4-32 | CH=N—NHCOOMe | CH₃ | H | |

TABLE 4-continued

Compounds of the formula (Id)

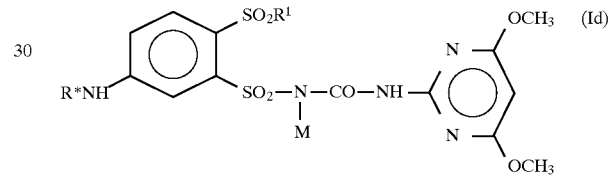

| Example number | R* | R¹ | M | m.p. |
|---|---|---|---|---|
| 4-33 | CH=N—NMe₂ | CH₃ | H | |
| 4-34 | CH=N—N⟨⟩ | CH₃ | H | |

TABLE 5

Compounds of the formula (Ie)

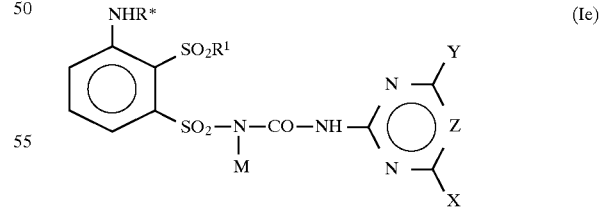

| Example number | R* | R¹ | M | X | Y | Z | m.p. |
|---|---|---|---|---|---|---|---|
| 5-1 | CHO | Me | H | OMe | OMe | CH | |
| 5-2 | CHO | Me | H | OMe | Me | CH | |
| 5-3 | CHO | Me | Na | OMe | Me | CH | |
| 5-4 | CHO | Me | Na | OMe | OMe | CH | |
| 5-5 | CHO | Et | H | OMe | OMe | CH | |
| 5-6 | CHO | Et | H | OMe | Me | CH | |
| 5-7 | CHO | Et | Na | OMe | Me | CH | |

TABLE 5-continued

Compounds of the formula (Ie)

(Ie) structure: benzene ring with NHR* substituent, SO₂R¹, and SO₂—N(M)—CO—NH— linked to a 6-membered ring with N, Y, Z, N, X positions.

| Example number | R* | R¹ | M | X | Y | Z | m.p. |
|---|---|---|---|---|---|---|---|
| 5-8 | CHO | Et | Na | OMe | OMe | CH | |
| 5-9 | CHO | ⁿPr | H | OMe | OMe | CH | |
| 5-10 | CHO | ⁿPr | H | OMe | Me | CH | |
| 5-11 | CHO | ⁿPr | Na | OMe | Me | CH | |
| 5-12 | CHO | ⁿPr | Na | OMe | OMe | CH | |
| 5-13 | CHO | ⁱPr | H | OMe | OMe | CH | |
| 5-14 | CHO | NMe₂ | H | OMe | OMe | N | |
| 5-15 | CHO | Me | H | OMe | OMe | N | |
| 5-16 | CHO | Me | H | OMe | Me | N | |
| 5-17 | CHO | Et | H | OMe | OMe | N | |
| 5-18 | CHO | Et | H | OMe | Me | N | |
| 5-19 | CHO | NMe₂ | H | OMe | OMe | N | |
| 5-20 | CHO | NMe₂ | H | OMe | Me | N | |
| 5-21 | CHO | ⁿPr | H | OMe | OMe | N | |
| 5-22 | CHO | ⁿPr | H | OMe | Me | N | |
| 5-23 | CHO | ⁱPr | H | OMe | OMe | N | |
| 5-24 | CHO | ⁱPr | H | OMe | Me | N | |

TABLE 6

Compounds of the formula (If)

(If) structure: benzene ring with SO₂R¹, NHR*, and SO₂—N(M)—CO—NH— linked to a 6-membered ring with N, Y, Z, N, X positions.

| Example number | R* | R¹ | M | X | Y | Z | m.p. |
|---|---|---|---|---|---|---|---|
| 6-1 | CHO | Me | H | OMe | OMe | CH | |
| 6-2 | CHO | Me | H | OMe | Me | CH | |
| 6-3 | CHO | Me | Na | OMe | Me | CH | |
| 6-4 | CHO | Me | Na | OMe | OMe | CH | |
| 6-5 | CHO | Et | H | OMe | OMe | CH | |
| 6-6 | CHO | Et | H | OMe | Me | CH | |
| 6-7 | CHO | Et | Na | OMe | Me | CH | |
| 6-8 | CHO | Et | Na | OMe | OMe | CH | |
| 6-9 | CHO | ⁿPr | H | OMe | OMe | CH | |
| 6-10 | CHO | ⁿPr | H | OMe | Me | CH | |
| 6-11 | CHO | ⁿPr | Na | OMe | Me | CH | |
| 6-12 | CHO | ⁿPr | Na | OMe | OMe | CH | |
| 6-13 | CHO | ⁱPr | H | OMe | OMe | CH | |
| 6-14 | CHO | NMe₂ | H | OMe | OMe | N | |
| 6-15 | CHO | Me | H | OMe | OMe | N | |
| 6-16 | CHO | Me | H | OMe | Me | N | |
| 6-17 | CHO | Et | H | OMe | OMe | N | |
| 6-18 | CHO | Et | H | OMe | Me | N | |
| 6-19 | CHO | NMe₂ | H | OMe | OMe | N | |
| 6-20 | CHO | NMe₂ | H | OMe | Me | N | |
| 6-21 | CHO | ⁿPr | H | OMe | OMe | N | |
| 6-22 | CHO | ⁿPr | H | OMe | Me | N | |
| 6-23 | CHO | ⁱPr | H | OMe | OMe | N | |
| 6-24 | CHO | ⁱPr | H | OMe | Me | N | |

TABLE 7

Compounds of the formula (Ig)

(Ig) structure: R*—NH— on benzene ring with SO₂R¹, and SO₂—N(M)—CO—NH— linked to a 6-membered ring with N, Y, Z, N, X positions.

| Example number | R* | R¹ | M | X | Y | Z | m.p. |
|---|---|---|---|---|---|---|---|
| 7-1 | CHO | Me | H | OMe | OMe | CH | |
| 7-2 | CHO | Me | H | OMe | Me | CH | |
| 7-3 | CHO | Me | Na | OMe | Me | CH | |
| 7-4 | CHO | Me | Na | OMe | OMe | CH | |
| 7-5 | CHO | Et | H | OMe | OMe | CH | |
| 7-6 | CHO | Et | H | OMe | Me | CH | |
| 7-7 | CHO | Et | Na | OMe | Me | CH | |
| 7-8 | CHO | Et | Na | OMe | OMe | CH | |
| 7-9 | CHO | ⁿPr | H | OMe | OMe | CH | |
| 7-10 | CHO | ⁿPr | H | OMe | Me | CH | |
| 7-11 | CHO | ⁿPr | Na | OMe | Me | CH | |
| 7-12 | CHO | ⁿPr | Na | OMe | OMe | CH | |
| 7-13 | CHO | ⁱPr | H | OMe | OMe | CH | |
| 7-14 | CHO | NMe₂ | H | OMe | OMe | N | |
| 7-15 | CHO | Me | H | OMe | OMe | N | |
| 7-16 | CHO | Me | H | OMe | Me | N | |
| 7-17 | CHO | Et | H | OMe | OMe | N | |
| 7-18 | CHO | Et | H | OMe | Me | N | |
| 7-19 | CHO | NMe₂ | H | OMe | OMe | N | |
| 7-20 | CHO | NMe₂ | H | OMe | Me | N | |
| 7-21 | CHO | ⁿPr | H | OMe | OMe | N | |
| 7-22 | CHO | ⁿPr | H | OMe | Me | N | |
| 7-23 | CHO | ⁱPr | H | OMe | OMe | N | |
| 7-24 | CHO | ⁱPr | H | OMe | Me | N | |

B. Formulation examples a) A dusting powder is obtained by mixing 10 parts by weight of a compound of the formula (I) and 90 parts by weight of talc, as the inert substance, and comminuting the mixture in an impact mill.

b) A wettable powder which is readily dispersible in water is obtained by mixing 25 parts by weight of a compound of the formula (I), 64 parts by weight of kaolin-containing quartz, as the inert substance, 10 parts by weight of potassium ligninsulfonate and 1 part by weight of sodium oleylmethyltauride, as the wetting and dispersing agent, and grinding the mixture in a pinned disk mill.

c) A dispersion concentrate which is readily dispersible in water is obtained by mixing 20 parts by weight of a compound of the formula (I) with 6 parts by weight of alkylphenol polyglycol ether (®Triton X 207), 3 parts by weight of isotridecanol polyglycol ether (8 EO) and 71 parts by weight of paraffinic mineral oil (boiling range, for example, about 255° to above 277° C.) and grinding the mixture to a fineness of less than 5 microns in a grinding bead mill.

d) An emulsifiable concentrate is obtained from 15 parts by weight of a compound of the formula (I), 75 parts by weight of cyclohexanone, as the solvent, and 10 parts by weight of oxyethylated nonylphenol, as the emulsifier.

e) Water-dispersible granules are obtained by mixing 75 parts by weight of a compound of the formula (I), 10 parts by weight of calcium ligninsulfonate, 5 parts by weight of sodium laurylsulfate, 3 parts by weight of polyvinyl alcohol and 7 parts by weight of kaolin, the mixture is ground on a pinned disk mill and the powder is granulated in a fluidized bed by spraying on water as the granulating liquid.

f) Water-dispersible granules are also obtained by homogenizing and precomminuting 25 parts by weight of a compound of the formula (I), 5 parts by weight of sodium 2,2'-dinaphthylmethane-6,6'-disulfonate, 2 parts by weight of sodium oleylmethyltauride, 1 part by weight of polyvinyl alcohol, 17 parts by weight of calcium carbonate and 50 parts by weight of water on a colloid mill, subsequently grinding the mixture on a bead mill and atomizing and drying the suspension thus obtained in a spray tower by means of a one-component nozzle.

C. Biological examples

1. Action on weeds by the pre-emergence method

Seeds or pieces of rhizome of monocotyledon and dicotyledon weed plants are laid out in sandy loam soil in plastic pots and covered with soil. The compounds according to the invention, formulated in the form of wettable powders or emulsion concentrates, are then applied to the surface of the covering soil as an aqueous suspension or emulsion in various dosages with an amount of water applied, when converted, of 600 to 800 l/ha.

After the treatment, the pots are placed in a greenhouse and are kept under good growth conditions for the weeds. The plant damage or emergence damage is rated visually after emergence of the test plants after a test period of 3 to 4 weeks in comparison with untreated controls. As the test results show, the compounds according to the invention have a good herbicidal pre-emergence activity against a broad spectrum of graminaceous weeds and broad-leaved weeds. For example, Examples no. 1-26, 2-26, 3-1, 3-13, 3-16, 3-26, 3-51, 3-76, 3-101 and 3-103 (cf. Tables 1 and 3) have a very good herbicidal action against harmful plants such as *Sinapis alba, Chrysanthemum segetum, Avena sativa, Stellaria media, Echinochloa crus-galli, Lolium multiflorum*, Setaria spp., *Abutilon theophrasti, Amaranthus retroflexus* and *Panicum miliaceum* in the pre-emergence method when applied in an amount of 0.3 kg or less of active substance per hectare.

2. Action on weeds by the post-emergence method

Seeds or pieces of rhizome of mono- and dicotyledon weeds are laid out in sandy loam soil in plastic pots, covered with soil and grown in a greenhouse under good growth conditions. Three weeks after sowing, the test plants are treated in the trifoliate stage. The compounds according to the invention, formulated as wettable powders or as emulsion concentrates, are sprayed onto the green parts of the plants in various dosages with an amount of water applied, when converted, of 600 to 800 l/ha. After the test plants have stood in the greenhouse under optimum growth conditions for about 3 to 4 weeks, the action of the preparations is rated visually in comparison with untreated controls. The compositions according to the invention also have a good herbicidal activity against a broad spectrum of economically important graminaceous weeds and broad-leaved weeds in the post-emergence method. For example, Examples no. 1-26, 2-26, 3-1, 3-13, 3-16, 3-26, 3-51, 3-76, 3-101 and 3-103 (cf. Tables 1 and 3) have a very good herbicidal action against harmful plants such as *Sinapis alba, Stellaria media, Echinochloa crus-galli, Lolium multiflorum, Chrysanthemum segetum*, Setaria spp., *Abutilon theophrasti, Amaranthus retroflexus, Panicum miliaceum* and *Avena sativa* in the post-emergence method when applied in an amount of 0.3 kg or less of active substance per hectare.

3. Crop plant tolerance

In further experiments in the greenhouse, seeds of a relatively large number of crop plants and weeds are laid out in sandy loam soil and covered with soil. Some of the pots are treated immediately as described under Section 1, and the others are placed in a greenhouse until the plants have developed two to three true leaves, and are then sprayed with the substances of the formula (I) according to the invention in various dosages as described under Section 2. Four to five weeks after the application and standing time in the greenhouse, it is found by visual rating that the compounds according to the invention leave dicotyledonous crops such as, for example, soya, cotton, rape, sugar beet and potatoes, undamaged by the pre- and post-emergence method even at high dosages of active compound. Some substances furthermore also protect graminaceous crops, such as, for example, barley, wheat, rye, sorghum, millet, maize or rice. Some of the compounds of the formula (I) have a high selectivity and are therefore suitable for controlling undesirable plant growth in agricultural crops.

We claim:

1. A compound of the formula (I) or a salt thereof

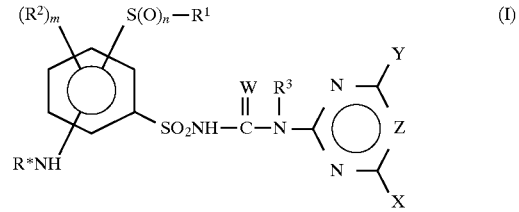

in which

W is an oxygen atom or a sulfur atom, m is 0, 1, 2 or 3, n is 0, 1 or 2,

R* is a radical of the formula —CHO, —CH=N—R or

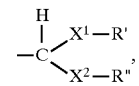

R is H, OH, $(C_1-C_6)$alkyl, $(C_2-C_6)$alkenyl, $(C_2-C_6)$alkynyl, $(C_1-C_6)$ alkoxy, $(C_2-C_6)$alkenyloxy or $(C_2-C_6)$alkynyloxy, where each of the last 6 radicals mentioned is unsubstituted or substituted, or is phenyl, which is unsubstituted or substituted, or acyl, amino or mono- or disubstituted amino, $X^1$ is O, S, NH or —N$((C_1-C_6)$alkyl)-[—N(alkyl)-], $X^2$ is O, S, NH or —N$((C_1-C_6)$alkyl)-[—N(alkyl)-], R' and R" independently of one another are hydrogen, $(C_1-C_6)$alkyl, $(C_2-C_6)$alkenyl or $(C_2-C_6)$alkynyl, where each of the last 3 radicals mentioned is unsubstituted or substituted by alkoxy, alkylthio or halogen, or together are $(C_2-C_4)$alkylene or $(C_2-C_4)$alkenylene, $R^1$ is hydroxyl, amino, mono- or disubstituted amino, hydroxylamino, substituted hydroxylamino, hydrazino, substituted hydrazino, a substituted or unsubstituted $(C_1-C_{12})$aliphatic hydrocarbon or hydrocarbonoxy radical or substituted or unsubstituted aryl or aryloxy from the group consisting of phenyl, naphthyl, tetrahydronaphthyl, indenyl, indanyl, pentalenyl, and fluorenyl, or substituted or unsubstituted heteroaryl or heteroaryloxy from the group consisting of pyridyl, pyrimidyl, pyridazinyl, pyrazinyl, thienyl, thiazolyl, oxazolyl, furyl, pyrrolyl, pyrazolyl and imidazolyl, $R^2$ is halogen, CN, $NO_2$, amino, mono- or disubstituted amino, alkyl or alkoxy, where each of the last two radicals mentioned is unsubstituted or substituted, $R^3$ is hydrogen, hydroxyl, $(C_1-C_4)$alkyl, $(C_1-C_4)$alkoxy, $(C_2-C_4)$alkenyl or $(C_2-C_4)$alkynyl, where each of the last 4 radicals mentioned is unsubstituted or substituted by halogen, X and Y independently of one another are hydrogen, hydroxyl, amino, mono- or disubstituted amino, $(C_1-C_6)$alkyl, $(C_3-C_7)$cycloalkyl, $(C_2-C_6)$alkenyl, $(C_2-C_6)$alkynyl, $(C_1-C_6)$alkoxy, $(C_2-C_6)$alkenyloxy, $(C_2-C_6)$alkynyloxy, $C_3-C_7$)cycloalkoxy or $(C_1-C_6)$alkylthio, where each of the last 9 radicals mentioned is unsubstituted or substituted, and is CH or

in which $R^o$ is halogen, cyano, $(C_1-C_6)$alkyl, $(C_1-C_6)$alkoxy, $(C_1-C_6)$haloalkyl or $(C_1-C_6)$haloalkoxy, wherein heterocyclyl means a heterocyclic radical having 3 to 7 ring atoms and containing one hetero unit from the group consisting of N, O, S, SO and $SO_2$, or a heterocyclic radical from the group consisting of pyrimidinyl, pyridazinyl, pyrazinyl, thiazolyl, oxazolyl, pyrazolyl, imidazolyl, dioxolanyl, morpholinyl, and piperazinyl and wherein substituted, if not further specified, means substituted with one or more substituents selected from the group consisting of halogen, alkoxy, haloalkoxy, alkylthiohyroxyl, amino, nitro, carboxyl, cyano, azido, alkoxycarbonyl, alkylcarbonyl, formyl, carbamoyl, mono- and dialkylaminocarbonyl, acylamino, mono-, dialkylamino, alkylsulfinyl, aloalkylsulfinyl, alkylsulfonyl, haloalkysulfonyl, and in case of cyclic radicals, alkyl, haloalkyl, alkenyl, alkynyl, alkenyloxy, and alkynyloxy, wherein radicals with carbon atoms have 1 to 4 carbon atoms, and wherein acylradical means a radical of a carboxylic acid, carboxylic acid of a thiocarboxylic acid, an optionally N-substituted iminocarboxylic acid, the radical of a carbonic acid monoester, an optionally N-substituted carbamic acid, a sulfonic acid, a sulfinic acid, phosphonic acid or a phosphinic acid, wherein radicals with carbon atoms have 1 to 12 carbon atoms, and wherein substituted amino, hydroxylamino or hydrazino means amino radicals which are N-substituted by one or two identical or different radicals from the group consisting of $(C_1-C_4)$alkyl, $(C_1-C_4)$alkoxy, acyl and substituted or unsubstituted phenyl.

2. A compound or a salt thereof as claimed in claim 1, in which

R* is a radical of the formula —CHO, —CH=N—R or

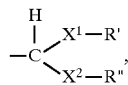

R is H, OH, $NH_2$, $(C_1-C_6)$alkyl, $(C_1-C_6)$haloalkyl, $(C_1-C_6)$alkoxy, $(C_1-C_6)$haloalkoxy, phenyl, which is unsubstituted or substituted, or $[(C_1-C_3)$-alkyl] carbonyl, $[(C_1-C_3)$alkoxy]carbonyl, aminocarbonyl, methylaminocarbonyl, dimethylaminocarbonyl, mono- or di$[(C_1-C_6)$-alkyl]amino, $[(C_1-C_3)$alkyl] carbonylamino, $[(C_1-C_3)$alkoxy]carbonylamino, aminocarbonylamino, methylaminocarbonylamino, dimethylaminocarbonylamino, $X^1$ is an oxygen atom, $X^2$ is an oxygen atom, R' and R" independently of one another are $(C_1-C_4)$alkyl, $R^1$ is OH, $NR^4R^5$, $(C_1-C_6)$alkyl, $(C_2-C_6)$alkenyl, $(C_2-C_6)$alkynyl, $(C_1-C_6)$alkoxy, $(C_2-C_6)$alkenoxy, $(C_2-C_6)$alkynoxy, $(C_3-C_7)$cycloalkyl, $(C_3-C_7)$cycloalkoxy, $(C_3-C_7)$cycloalkyl$(C_1-C_2)$alkyl, $(C_3-C_7)$cycloalkyl$(C_1-C_4)$alkoxy, phenoxy, phenyl, thienyl or pyridyl, where each of the last fifteen radicals mentioned is unsubstituted or substituted by one or more radicals from the group consisting of halogen, $(C_1-C_4)$alkoxy, $(C_1-C_4)$haloalkyl, $(C_2-C_4)$alkenoxy, $(C_2-C_4)$haloalkenoxy, $(C_2-C_4)$alkynoxy, $(C_2-C_4)$haloalkynoxy, CN, $NO_2$, $N_3$, SCN, OCN, OH, $NR^6R^7$, CO—$R^8$, $(C_1-C_4)$alkylthio, $(C_1-C_4)$haloalkylthio, unsubstituted and substituted phenyl, SO—$R^9$ and $SO_2R^{10}$, and in the case of cyclic radicals also $(C_1-C_4)$alkyl and $(C_1-C_4)$haloalkyl, $R^2$ is halogen, $(C_1-C_3)$alkyl, $(C_1-C_3)$haloalkyl, $(C_1-C_5)$alkoxyalkyl, $NO_2$, $NR^{11}R^{12}$, CN, $(C_1-C_3)$alkoxy or $(C_1-C_3)$haloalkoxy, $R^3$ is H, OH, $(C_1-C_3)$alkyl, $(C_2-C_3)$alkenyl, $(C_2-C_3)$alkynyl or $(C_1-C_3)$alkoxy, $R^4$ is H, OH, $NH_2$, mono- and di$[(C_1-C_3)$alkyl]amino, $(C_1-C_4)$alkyl, $(C_2-C_4)$alkenyl, $(C_2-C_4)$alkynyl, $(C_1-C_4)$alkoxy, $(C_2-C_4)$alkenoxy, $(C_2-C_4)$alkynoxy, where each of the last eight radicals mentioned is unsubstituted or substituted by one or more radicals from the group consisting of halogen, $(C_1-C_3)$alkoxy, $(C_1-C_3)$haloalkoxy, $(C_1-C_3)$alkylthio and $(C_1-C_3)$haloalkylthio, and $R^5$ is H, $(C_1-C_4)$alkyl, $(C_2-C_4)$alkenyl, $(C_2-C_4)$alkynyl, $[(C_1-C_4)$alkyl]carbonyl, $[(C_2-C_4)$alkenyl]carbonyl, $[(C_1-C_4)$alkoxy]carbonyl, $[(C_2-C_4)$alkenoxy]carbonyl, $[(C_1-C_4)$alkyl]aminocarbonyl, di$[(C_1-C_4)$alkyl]aminocarbonyl, $(C_1-C_4)$alkylsulfonyl, $(C_2-C_4)$alkenylsulfonyl, $(C_1-C_4)$alkylaminosulfonyl or di$[(C_1-C_4)$alkyl]aminosulfonyl, where each of the last thirteen radicals mentioned is unsubstituted or substituted by one or more radicals from the group consisting of halogen, OH, $(C_1-C_3)$alkoxy, $(C_1-C_3)$haloalkoxy, $(C_1-C_3)$alkylthio and $(C_1-C_3)$haloalkylthio, or $NR^4R^5$ together is heterocyclic radical from the group consisting of piperidine, morpholine, piperazine and pyrrolidine which is unsubstituted or substituted by one or more radicals from the group consisting of the oxo function, halogen, OH, $NH_2$, $NO_2$, $NHCH_3$, $N(CH_3)_2$, CN, $CONH_2$, $CONHCH_3$, CO—$OCH_3$, $CON(CH_3)_2$, $COCH_3$, CO—H, $(C_1-C_3)$alkyl, $(C_1-C_3)$haloalkyl, $(C_1-C_3)$alkoxy and $(C_1-C_3)$haloalkoxy, $R^6$ is H, $(C_1-C_4)$alkyl, $(C_1-C_4)$haloalkyl, $(C_2-C_4)$alkenyl, $(C_2-C_4)$haloalkenyl, $(C_2-C_4)$alkynyl, $(C_2-C_4)$haloalkynyl, OH, $(C_1-C_3)$alkoxy or $(C_2-C_3)$haloalkoxy and $R^7$ is H, $(C_1-C_4)$alkyl, $(C_1-C_4)$haloalkyl, $(C_2-C_4)$alkenyl, $(C_2-C_4)$haloalkenyl, $(C_2-C_4)$alkynyl, $(C_2-C_4)$haloalkynyl, CO—H, $CO_2CH_3$, CO—$CH_3$, CO—$NH_2$, CO—$NHCH_3$ or $CON(CH_3)_2$, or $NR^6R^7$ together is a heterocyclic radical from the group consisting of piperidine, morpholine, piperazine and pyrrolidine which is unsubstituted or substituted by one or more radicals from the group consisting of halogen, OH, $NH_2$, $NO_2$, $CONHCH_3$, $CONH_2$, $NHCH_3$, $N(CH_3)_2$, CN, $CO_2CH_3$, $CON(CH_3)_2$, $COCH_3$, CO—H, $(C_1-C_3)$alkyl, $(C_1-C_3)$haloalkyl, $(C_1-C_3)$alkoxy, $(C_1-C_3)$haloalkoxy and the oxo function, $R^8$ is H, $(C_1-C_3)$alkyl, $(C_1-C_3)$haloalkyl, $(C_1-C_3)$alkoxy, $(C_1-C_3)$haloalkoxy, $(C_1-C_3)$alkythio, $(C_1-C_3)$haloalkylthio, $NH_2$, $NHCH_3$, $N(CH_3)_2$ or OH, $R^9$ is $(C_1-C_4)$alkyl, $(C_1-C_4)$haloalkyl, $(C_2-C_5)$alkoxyalkyl, $(C_2-C_4)$alkenyl, $(C_2-C_4)$haloalkenyl, $(C_2-C_4)$alkynyl or $(C_2-C_4)$haloalkynyl, $R^{10}$ is $(C_1-C_4)$alkyl, $(C_1-C_4)$haloalkyl, $(C_2-C_4)$alkenyl, $(C_2-C_5)$haloalkyl, $(C_1-C_4)$alkoxy, $(C_1-C_4)$haloalkoxy, $(C_2-C_4)$alkenoxy, $(C_2-C_4)$haloalkenoxy, $NH_2$, mono- or di[$(C_1-C_4)$alkyl]amino, $R^{11}$ is H, $(C_1-C_3)$alkyl, $(C_1-C_3)$haloalkyl, $(C_1-C_3)$alkoxy, $(C_1-C_3)$haloalkoxy or OH and $R^{12}$ is H, $(C_1-C_3)$alkyl, $(C_1-C_3)$haloalkyl, CHO, $COCH_3$, $CO_2CH_3$, $CO_2C_2H_5$, $SO_2CH_3$ or CN, or $NR^{11}R^{12}$ together is a heterocyclic radical from the group consisting of piperidine, morpholine, piperazine and pyrrolidine which is unsubstituted or substituted by one or more radicals from the group consisting of halogen, OH, $NH_2$, $NO_2$, $NHCH_3$, $N(CH_3)_2$, CN, $CONHCH_3$, $CO_2CH_3$, $COCH_3$, $CON(CH_3)_2$, CO—H, $(C_1-C_3)$alkyl, $CONH_2$, $(C_1-C_3)$alkoxy, $(C_1-C_3)$haloalkyl, $(C_1-C_3)$haloalkoxy and the oxo function, X and Y independently of one another are H, halogen, $(C_1-C_6)$alkyl, $(C_1-C_6)$alkoxy, $(C_1-C_6)$alkylthio, $(C_3-C_7)$cycloalkyl, $(C_2-C_6)$alkenyl, $(C_2-C_6)$alkynyl, $(C_2-C_6)$alkynyloxy or mono- or di[$(C_1-C_4)$alkyl] amino, where each of the last nine radicals mentioned is unsubstituted or substituted by one or more radicals from the group consisting of halogen, $(C_1-C_4)$alkoxy, $(C_1-C_4)$haloalkoxy, $(C_1-C_4)$alkylthio and $(C_1-C_4)$haloalkylthio, and Z is CH or N.

3. A compound or a salt thereof as claimed in claim 1, in which $R^1$ is $(C_1-C_4)$alkyl, $(C_2-C_4)$alkenyl, $(C_2-C_4)$alkynyl or $(C_1-C_4)$alkoxy, where each of the last 4 radicals mentioned is unsubstituted or substituted by one or more radicals from the group consisting of halogen, $(C_1-C_4)$alkoxy and $(C_1-C_4)$alkylthio, or is $(C_3-C_6)$cycloalkyl, benzyl, phenyl, thienyl or pyridyl, where each of the last 5 radicals mentioned is unsubstituted or substituted by one or more radicals from the group consisting of halogen, $(C_1-C_4)$alkyl, $(C_1-C_4)$alkoxy, $(C_1-C_4)$haloalkyl, $(C_1-C_4)$haloalkoxy, CN, $NO_2$ and OH, or is $NH_2$ or mono- or di[$(C_1-C_4)$alkyl]amino, n is 0, 1 or 2, $R^2$ is $(C_1-C_4)$alkyl, $(C_1-C_4)$alkoxy or halogen, m is 0, 1, 2 or 3, one of the radicals X and Y is halogen, $(C_1-C_4)$alkyl, $(C_1-C_4)$alkoxy, $(C_1-C_4)$haloalkyl, $(C_1-C_4)$haloalkoxy or mono- or di[$(C_1-C_4)$alkyl]amino and the other of the radicals X and Y is $(C_1-C_4)$alkyl, $(C_1-C_4)$alkoxy or $(C_1-C_4)$haloalkoxy.

4. A herbicidal or plant growth-regulating composition which comprises one or more compound of the formula (I) or a salt thereof as claimed in claim 1, and formulating auxiliaries customary in plant protection.

5. A method of controlling harmful plants or of regulating the growth of plants, wherein an effective amount of a compound of the formula (I) or of a salt thereof as claimed in claim 1 is used as a herbicide or plant growth regulator.

6. A method as claimed in claim 6, wherein an effective amount of one or more compounds of the formula (I) or of a salt thereof is applied to the plants, their plant seeds or the area on which they grow.

* * * * *